(12) United States Patent
Kamerling et al.

(10) Patent No.: US 11,497,934 B2
(45) Date of Patent: Nov. 15, 2022

(54) METHOD FOR TREATMENT OF MULTIPLE BRAIN METASTASES BASED ON ISO-DOSE LINE PRESCRIPTIONS

(71) Applicant: Brainlab AG, Munich (DE)

(72) Inventors: Cornelis Kamerling, Poing (DE); Stefan Schell, Munich (DE); Andreas Schatti, Chur (CH)

(73) Assignee: Brainlab AG, Munich (DE)

( * ) Notice: Subject to any disclaimer, the term of this patent is extended or adjusted under 35 U.S.C. 154(b) by 932 days.

(21) Appl. No.: 16/302,008

(22) PCT Filed: Oct. 27, 2017

(86) PCT No.: PCT/EP2017/077640
§ 371 (c)(1),
(2) Date: Nov. 15, 2018

(87) PCT Pub. No.: WO2019/081042
PCT Pub. Date: May 2, 2019

(65) Prior Publication Data
US 2021/0220673 A1 Jul. 22, 2021

(51) Int. Cl.
*A61N 5/10* (2006.01)
*G16H 20/40* (2018.01)
(Continued)

(52) U.S. Cl.
CPC ......... *A61N 5/1039* (2013.01); *A61N 5/1047* (2013.01); *A61N 5/1049* (2013.01);
(Continued)

(58) Field of Classification Search
CPC .............. A61B 2034/107; A61N 5/103; A61N 5/1039; A61N 5/1047; A61N 5/1049
See application file for complete search history.

(56) References Cited

U.S. PATENT DOCUMENTS 9,764,162 B1* 9/2017 Willcut ................ G06T 7/0014
2004/0146141 A1* 7/2004 Svatos .................... A61N 5/103
378/65

(Continued)

FOREIGN PATENT DOCUMENTS

WO WO2013075743 A1 5/2013
WO WO2015039903 A1 3/2015

OTHER PUBLICATIONS

Vassil et al. "General Physics Principles". Handbook of Treatment Planning in Radiation Oncology. Aug. 31, 2010.
Khan et al. "Chapter 11: Treatment Planning I: Isodose Distributions" and "Chapter 12: Treatment Planning II: Patient Data, Corrections, and Setup". Khan's Lectures: Handbook of the Physics of Radiation Therapy. Jun. 27, 2011.
(Continued)

*Primary Examiner* — Christine H Matthews
(74) *Attorney, Agent, or Firm* — Middleton Reutlinger

(57) ABSTRACT

Disclosed is a computer-implemented method of determining a treatment plan, encompassing acquiring patient image data, acquiring target data describing targets, acquiring position data describing control points which define one or more arcs, and determining target projection data which describes outlines of the target in a beam's-eye view. Margin data is acquired. For the outlines, margins are applied to determine auxiliary outlines. Beam shaping device data is determined describing configurations of the collimator leaves so that irradiation of the auxiliary outlines is enabled. Based on these configurations, the irradiation amount is simulated for voxels of the patient image data. Constraints to be fulfilled by the treatment plan may be set. Configurations of blockings, arc-weights and margins are proposed. Only different combinations of these parameters are proposed while additional possible parameters are neglected. An optimization algorithm is used to minimize an objective function. The best configuration is selected as the treatment plan.

15 Claims, 6 Drawing Sheets

(51) Int. Cl.
  *G16H 50/50*   (2018.01)
  *G16H 30/20*   (2018.01)
  *G16H 40/63*   (2018.01)

(52) U.S. Cl.
  CPC ............ *G16H 20/40* (2018.01); *G16H 30/20* (2018.01); *G16H 40/63* (2018.01); *G16H 50/50* (2018.01)

(56) References Cited

U.S. PATENT DOCUMENTS

2004/0165696 A1  8/2004  Lee
2008/0123813 A1  5/2008  Maurer et al.

OTHER PUBLICATIONS

Gill et al. "Determination of Optimal PTV Margin for Patients Receiving CBCT-Guiding Prostate IMRT: Comparative Analysis Based on CBCT Dose Calculation with Four Different Margins". Journal of Applied Clinical Medical Physics. vol. 16, No. 6. Nov. 30, 2015.
International Search Report and Written Opinion issued in PCT Application No. PCT/EP2017/077640 dated Jul. 23, 2018.
Lau et al. "Single-Isocenter Frameless Volumetric Modulated Arc Radiosurgery for Multiple Intracranial Metastases". Neurosurgery. Aug. 1, 2016.
Kang et al. "A Method for Optimizing LINAC Treatment Geometry for Volumetric Modulated Arc Therapy of Multiple Brain Metastases". Medical Physics Journal. vol. 37, No. 8. Jul. 20, 2010.

\* cited by examiner

METHOD FOR TREATMENT OF MULTIPLE BRAIN METASTASES BASED ON ISO-DOSE LINE PRESCRIPTIONS

FIELD OF THE INVENTION

The present invention relates to a computer-implemented method for determining a treatment plan, a corresponding computer program, and a non-transitory program storage medium storing such a program and a computer for executing the program, as well as a medical system comprising an electronic data storage device and the aforementioned computer.

TECHNICAL BACKGROUND

The method aims to provide advanced treatment planning for (e.g. multiple) brain metastases including iso-dose line (IDL) prescriptions, allowing the operator to control dose homogeneity/inhomogeneity by prescribing a range of dose values per treated metastasis, and risk structure sparing, allowing the operator to reduce dose in specified volumes of interest.

There are known solutions for multiple brain metastases treatment planning which lack support for IDL prescriptions and risk structure sparing. The algorithm from previous solutions for multiple brain metastases treatment planning could not be extended to the aim of the method described above. Dose prescription was limited to a single dose prescription value, controlling dose constraints to risk structures was lacking and the optimization process could not be influenced by the operator.

One can differentiate between three tissue types: target volumes (e.g. the volumes of interest containing the brain tumors and metastases which are selected for treatment by irradiation), surrounding normal tissue (e.g. the volume of the patient's head) and risk structures (e.g. pre-defined volumes of interest, typically corresponding to vital organs such as brainstem, eye and optical nerve).

The aim of treatment planning is to find an irradiation plan which delivers the prescribed dose values to the target volumes. The dose to surrounding normal tissue may be limited. Moreover, dose limits can be set for risk structures, to constrain dose to the respective localities.

The present invention can be used for radiotherapy or radiosurgery procedures e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses acquiring patient image data describing anatomical body parts of a patient, acquiring target data describing targets (metastases), acquiring position data describing control points which define one or more paths (arcs), and determining target projection data which describes outlines of the metastases in a beam's-eye view. Margin data is acquired (e.g. −1 mm, 0 mm, +0.5 mm, +1 mm . . . ). For each of the outlines, the margins are applied to determine so-called auxiliary outlines. Then, beam shaping device data is determined for all control points, all targets and all margins. This beam shaping device data describes configurations of the collimator leaves so that irradiation of irradiation areas defined by the auxiliary outlines is enabled (e.g. projection of targets including margins onto the collimator to determine required collimator shape). Based on the configurations of the collimator leaves, the irradiation dose can be simulated for individual voxels of the patient image data.

A user may specify constraints to be fulfilled by the treatment plan, for example a lower dose prescription limit, an upper dose prescription limit and a risk structure dose limit. The user may set these limits for individual targets and risk structures.

Several configurations of blockings, arc-weights and margins are proposed heuristically and randomly. Only different combinations of these parameters are proposed while additional possible parameters (e.g. control of individual collimator leaves independent of the outlines) are neglected. An optimization algorithm is used to minimize an objective function. The objective function describes deviations of simulated irradiation doses received by the voxels of the patient image data when using a proposed configuration, from the constraints set by the user. Additionally, the objective function includes the gradient index and the sum of all arc weights, which both shall be minimized resulting in the selection of a treatment plan

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining a treatment plan.

The treatment plan is for example determined for treating at least one target. The target may be a tumor, a metastasis or else. The treating of the at least one target may be performed by emitting irradiation by a beam source. The emission of the treatment beam is not part of the claimed method which rather relates to the determination of the treatment plan. The irradiation is for example performed by a beam source such as a linear accelerator, a circular accelerator, a radioactive isotope or else. The irradiation is for example emitted by the beam source through a beam shaping device which for example comprises at least one of collimator leaves, components opaque for the irradiation of the beam source, (electromagnetic) lenses and filters. The irradiation is emitted in an irradiation direction movable around a preferably movable patient support device. The irradiation direction can be simulated without controlling the treatment device to emit the irradiation.

The irradiation direction is for example movable around a fixed patient support device. It is for example movable around a movable patient support device. In any case, the positional relationship between the irradiation direction and the patient support device can be changed e.g. by moving the patient support device and/or the irradiation direction. The irradiation direction may be changed by moving the beam source, by moving the beam shaping device or by controlling the beam shaping device so as to change the irradiation direction.

For example, the patient support device comprises a patient couch supporting the patient. The patient support device may alternatively or additionally comprise a robotic positioning device which is configured to position the patient.

The treatment plan for example specifies one or more paths along which the irradiation direction and/or the patient support device shall move during irradiation. These paths are also referred to as "arcs". For example, the one or more paths are each specified by one or more control points. For example, the one or more control points define several relative positions between the patient support device and the irradiation direction. Directions of movement to be performed by the irradiation direction relative to the patient support device may be determined only by the control points. For example, the irradiation direction moves in relation to the patient support device from one control point to a subsequent control point (the control points may be in a specified order) along the shortest possible way. It may also move from one control point to another using interpolation between the control points. It may also move from one control point to another while avoiding abrupt changes in movement direction and/or speed. Other ways of controlling the movement based on the control points are possible.

The treatment plan for example specifies, for each of the one or more paths, (a number of) monitor units to be emitted by the beam source during movement along the each of the one or more paths. The (number of) monitor units are the amount of irradiation emitted by the beam source at a given control point. For example, the (number of) monitor units may differ from one control point to another. The (number of) monitor units may be the same for all control points of a path (arc). For example, the (number of) monitor units may be the same for all control points of a path (arc) whilst the time during which the beam source emits the irradiation at a given control point differs from one control point to another. For example, the (number of) monitor units are the same for all control points of a path (arc) whilst the time during which the beam source emits the irradiation is the same for all control points of the path (arc).

The treatment plan for example specifies the configuration of the beam shaping device. The configuration of the beam shaping device for example influences the shape of the beam of irradiation emitted by the beam source, when passing through the beam shaping device. For example, the cross-sectional shape of the beam is controlled by the configuration of the beam shaping device. For example, the cross-sectional intensity distribution of the beam is controlled by the configuration of the beam shaping device (e.g. focusing, scattering, change in transverse (cross-sectional) intensity profile). For example, the configuration of the beam shaping device includes information of controlling the beam shaping device. The configuration of the beam shaping device is for example specified by positions of elements which at least partly block the irradiation. In the case of a (multi-)leaf collimator as the beam shaping device, the configuration may be determined by the position(s) of the collimator leaf(s). The configuration of the beam shaping device is for example specified by electric fields controlled by the beam shaping device.

For example, the treatment plan specifies the configuration of the beam shaping device for one or more of the control points, for example for each of the control points (all control points) of the treatment plan. For example, the configuration of the beam shaping device may be different for different control points. It may be the same for several control points.

The method comprises executing, on at least one processor of at least one computer (for example at least one computer being part of a navigation and/or radiotherapy and/or radiosurgery system), the following exemplary steps which are executed by the at least one processor.

In a (for example first) exemplary step, patient image data is acquired. The patient image data may comprise one or more two-dimensional images and/or one or more three-dimensional images. For example, the patient image data comprises a stack of 2D images. For example, voxels can be generated from the patient image data. In the case of a single 2D image, each pixel may be specified to have a predetermined depth, for example a depth defining a cubic voxel. In the case of a stack of 2D images, the same approach could be used. Alternatively, each pixel comprised in a first 2D image of the stack of 2D images may be specified to have a depth corresponding to the distance from the first 2D image to a second 2D image of the stack of 2D images, wherein the first and the second 2D image may be neighboring images in the stack. In the case of 3D images, voxels are defined in the image data directly and do not need to be determined on the basis of one or more 2D images.

The patient image data for example describes one or more anatomical body parts of a patient. For example, the one or more anatomical body parts are parts of the patient's body. For example, at least one of the one or more anatomic body parts corresponds to an entire anatomic organ. For example, at least one of the one or more anatomic body parts of the patient corresponds to an arbitrary three-dimensional part of the patient, which is for example part of one or more anatomic organs.

In a (for example second) exemplary step, target data is acquired. For example, the target data is determined based on a user input and based on the patient image data. For example, the target data is linked to the patient image data. For example, the target data and the patient image data use the same reference system (the first reference system).

The target data for example specifies at least one of the one or more anatomical body parts as at least one target for irradiation. For example, the target data indicates a geometry (shape and/or position) of the at least one target, for example in the first reference system. For example, the target data indicates a geometry in the patient image data which is specified as the at least one target for irradiation. The target data for example specifies a first group of at least one of the one or more anatomical body parts as a first target, a second group of the at least one of the one or more anatomical body parts as a second target and son on. For example, different targets comprise different anatomical body parts. For example, each of the one or more anatomical body parts is only comprised in a single target.

In a (for example third) exemplary step, position data is acquired. The position data may be dependent on the treatment device (specific for a given combination of the patient treatment device and the possible irradiation directions). The position data may be based on the possible irradiation directions and the possible positions of the patient support device. For example, the one or more control points are one or more of the at least one position of the patient support device in relation to the irradiation direction described by the position data.

The position data for example describes at least one position of the patient support device in relation to the irradiation direction. For example, the position data describes a position of the patient support device in a second reference system and an irradiation direction in a third reference system as well as a transformation describing the relation between the second and the third reference system. The position data for example additionally describes a transformation between the first reference system of the patient image data and the second reference system of the patient support device or a transformation between the first reference system and the third reference system of the irradiation direction. For example, the position data describes (only) the control points specifying the one or more paths specified by the treatment plan. Also in this case, the position data for example further describes transformations between the first, second and third reference system.

In a (for example fourth) exemplary step, target projection data is determined. The target projection data is for example determined based on the target data and the position data. For example, the at least one target is indicated in the first reference system and transformed into the second reference system using a transformation indicated by the position data.

The target projection data is for example determined for at least one target. For example, it is determined for all targets described by the target data. For example, it is determined for a predetermined set of targets being a smaller subset of the at least one target.

The target projection data is for example determined for at least one position of the patient support device in relation to the irradiation direction. The at least one position is for example specified as a position of the patient support device in the second reference system and a position of the irradiation direction in a third reference system. The at least one position is for example specified as a transformation between the second and the third reference system. The at least one position is for example described by the position data. The at least one position for example is a smaller subset of the positions described by the position data. The at least one position for example corresponds to all positions described by the position data.

For example, the target projection data describes an outline of the at least one target projected into a plane perpendicular to a simulated beam direction. The simulated beam direction is for example specified by the position of the patient support device in relation to the irradiation direction. For example, the position data describes a transformation between the first and the second reference system. The one or more anatomical body parts described by the patient image and the targets described by the target data are for example transformed from the first reference system into the second reference system based on the position data indicating a transformation between the first and the second reference system. The simulated beam direction is for example determined based on the irradiation direction in the third reference system and a transformation between the second and the third reference system. For example, the simulated beam direction is transformed from the third reference system into the second reference system based on a transformation indicated by the position data to obtain the simulated beam direction.

The simulated beam direction is for example different for different relative positions between the patient support device and the irradiation direction. The simulated beam direction can for example be described as a direction from which a treatment beam (irradiation emitted by the beam source after passing the beam shaping device) would hit the patient in case the patient was positioned on the patient support device and the relative position between the patient and the patient support device was known (transformation between the first and the second reference system).

As noted above, the simulated beam direction is for example different for different positions between the patient support device and the irradiation direction. In this case, as noted above, the first patient image data is for example transformed from the first reference system into the second reference system. For example, the transformation between the first and the second reference system is kept fixed at all times while the position of the patient support device and the position of the irradiation direction may change. For example, the transformation between the first and the second reference system is kept fixed whilst the transformation between the second and the third reference system is variable depending on the relative positions between the patient support device and the irradiation direction, which relative positions are for example indicated by the position data.

The at least one target (or one or more of the at least one target) are for example projected into a plane to obtain the corresponding outline. For example, the at least one target is projected using a parallel projection. For example, the at least one target is projected using a parallel projection and an additional size (and/or shape) adjustment to enlarge or shrink the projected outline. For example, the size (and/or shape) adjustment is performed based on boundary conditions defined by the beam source and/or the beam shaping device. For example, the cross-section of an emitted irradiation beam may change depending on the distance from the beam source and/or the beam shaping device. To take this variation into account, the size (and/or shape) adjustment may be performed, for example.

Each outline for example represents a two-dimensional geometry (shape and position) which encloses all parts of the corresponding target. Each outline for example represents a two-dimensional geometry (shape and position) which encloses a predetermined amount of the corresponding target, for example all parts of the corresponding target which have more than a predetermined (e.g. acquired) number of voxels projected onto a same region (e.g. a same pixel) of the plane (all parts of the corresponding target which have more than a predetermined (e.g. acquired) thickness in the simulated beam's-eye-view). For example, a projection of a target into the plane leads to a single two-dimensional geometry. The outline is for example described in the second reference system. The outline is for example described in the first reference system.

The plane into which the at least one target is projected is for example perpendicular to the simulated beam direction. In this case, the outline of a projected target can for example be described as a two-dimensional representation of the target as seen from the direction of the simulated beam (simulated beam's-eye-view). For example, all of the at least one target are projected into the same plane. For example, the simulated beam direction is a normal (normal vector) to the plane into which the at least one target is projected.

In a (for example fifth) exemplary step, margin data is acquired. The margin data is for example valid for all of the at least one target. The margin data is for example target-specific.

The margin data for example describes one or more margins for the at least one target. In case the margin data is valid for all of the at least one target, the margins may be the same for all of the at least one target. In case the margin data is target-specific, the one or more margins are for example different for different targets.

For example, a margin is a distance of an outline of the at least one projected target to an auxiliary outline correlated with the at least one target. For example, a margin is a distance of an outline of a first projected target to a first auxiliary outline correlated with the first projected target.

For example, a margin is a distance of an outline of a second projected target to a second auxiliary outline correlated with the second projected target.

The term correlated for example encompasses a link between the auxiliary outline and the corresponding target. For example, a first target is linked to at least one of a first relative position between the patient support device and the irradiation direction, a first outline for the first relative position between the patient support device and the irradiation direction, a first margin, and a first auxiliary outline for the first outline and the first margin. For example, the first auxiliary outline is linked with the first target. For example, the first target, the first relative position between the patient support device and the irradiation direction, the first outline the first margin, and the first auxiliary outline are linked to one another such that each of these components can be obtained when referring to only one of these components individually.

The auxiliary outline of a specific target is for example determined by performing size adjustment to enlarge or shrink the outline of the specific target. The size adjustment for example comprises enlarging or shrinking the outline for a spatial amount described by the margin data (e.g. 0 mm, 0.1 mm, 0.5 mm, 0.75 mm, 0.8 mm, 0.85 mm, 1 mm, 1.5 mm or else). The auxiliary outline correlated with a specific target for example is a geometry (for example a two-dimensional geometry (shape and position)) having a constant spatial distance to the outline (which for example is a two-dimensional geometry) of the specific target. The constant spatial distance is for example called a margin. The margin data for example describes at least one negative margin (e.g. −0.1 mm, −0.5 mm, −0.75 mm, −0.8 mm, −0.85 mm, −1 mm, −1.5 mm or else). A negative margin for example indicates shrinking the outline of a target to obtain the auxiliary outline. In this case, the auxiliary outline is for example inside the outline. For example, the auxiliary outline is a two-dimensional geometry which is completely enclosed in the outline, wherein the outline for example also is a two-dimensional geometry. The margin data for example describes at least one positive margin (e.g. 0.1 mm, 0.5 mm, 0.75 mm, 0.8 mm, 0.85 mm, 1 mm, 1.5 mm or else). A positive margin for example indicates enlarging the outline of a target. An auxiliary outline is for example defined in the same reference system as the outline of the corresponding target. A margin which is equal to 0 mm for example indicates an auxiliary outline which is equal to the outline of the correlated target (the target used to determine the outline and, based on the outline, determine the auxiliary outline).

In a (for example sixth) exemplary step, auxiliary outline data is determined. For example, the auxiliary outline data is determined based on the target projection data and the margin data. The auxiliary outline data is for example determined for the at least one target. The auxiliary outline data is for example determined for all of the at least one target.

The auxiliary outline data is for example determined for at least one position of the patient support device in relation to the irradiation direction. For example, the auxiliary outline data is determined for all positions of the patient support device in relation to the irradiation direction which were used to determine the outline of the at least one target.

The auxiliary outline data is for example determined for one or more margins. For example, the auxiliary outline data is determined for all margins described by the margin data. For example, the auxiliary outline data is determined for each of the at least one target individually. For example, the auxiliary outline data is determined for each target individually, using target-specific margins described by the margin data.

The auxiliary outline data for example describes one or more auxiliary outlines correlated with the at least one target. For example, the auxiliary outline data describes all determined auxiliary outlines. For example, the auxiliary outline data describes at least one auxiliary outline which is linked to (e.g. correlated with) the at least one target used to obtain the outline used to obtain the auxiliary outline. For example, other links may be used as described above.

In a (for example seventh) exemplary step, beam shaping device data is determined. For example, the beam shaping device data is determined based on the auxiliary outline data. For example, the beam shaping device data is determined furthermore based on one or more boundary conditions of the beam source and/or the beam shaping device (e.g. size and number of irradiation-blocking components (for example collimator leaves), opacity of irradiation-blocking components, maximum irradiation beam cross-section, minimum irradiation beam cross-section and so on). The one or more boundary conditions are for example described by boundary condition data. The boundary condition data is for example acquired before determining the beam shaping device data. For example, the beam shaping device data is determined based on the auxiliary outline data such that irradiation of one or more irradiation areas specified by the one or more auxiliary outlines would be enabled in case of actually performing the irradiation. The beam shaping device data for example describes configurations of the beam shaping device which enable irradiation of one or more irradiation areas specified by the one or more auxiliary outlines. For example, the beam shaping device data is determined for all irradiation areas specified by all auxiliary outlines described by the auxiliary outline data.

For example, an irradiation area is defined as an area surrounded by an auxiliary outline. For example, an irradiation area is a two-dimensional geometry which is limited at the outermost border by an auxiliary outline, wherein the two-dimensional geometry lies in a plane, for example the plane into which the at least one target is projected to determine the outlines and/or the same plane in which the auxiliary outline lies. For example, an irradiation area is defined in the same reference system as the auxiliary outline(s) and/or in the same reference system as the outline(s), for example in the first reference system and/or in the second reference system.

In a (for example eighth) exemplary step, irradiation data is determined. The irradiation data is for example determined based on the patient image data and the beam shaping device data. The irradiation data is for example determined for at least one voxel of the patient image data. The irradiation data is for example determined for all voxels of the patient image data. As noted above, voxels can for example be generated for the patient image data in case of a single two-dimensional patient image and in case of a plurality (a stack) of two-dimensional patient images. For example, voxels are generated from multiple two-dimensional images in the same manner as when generating a cone-beam computed tomography (CBCT) out of multiple images of a patient.

The irradiation data describes the simulated irradiation dose for example for each configuration of the beam shaping device described by the beam shaping device data. The irradiation data is for example determined for one or more configurations of the beam shaping device. The irradiation data is for example determined for all configurations of the beam shaping device described by the beam shaping device data. The irradiation data is for example determined for all configurations of the beam shaping device which were determined based on the auxiliary outline data. For example, the irradiation data is determined for each of the one or more configurations of the beam shaping device individually. The irradiation data is for example determined for all of the one or more auxiliary outlines described by the auxiliary outline data, for example individually. The irradiation data for example describes a simulated irradiation dose received by the at least one voxel. The simulated irradiation dose received by one of the at least one voxel is for example different than the simulated irradiation dose received by another one of the at least one voxel (different irradiation doses for different voxels). For example, the irradiation data describes the simulated irradiation dose received by the at least one voxel, for each of the at least one voxel individually. For example, the simulated irradiation dose is determined based on a predetermined number of monitor units to be emitted by the beam source at a given relative position between the patient support device and the irradiation direction. For example, for determining the simulated irradiation dose, a predetermined number of monitor units is used for all relative positions between the patient support device and the irradiation direction. For example, the simulated irradiation dose depends linearly (or is regarded as depending linearly) on the number of monitor units to be emitted by the beam source.

In a (for example ninth) exemplary step, constraint data is acquired. For example, the constraint data describes criteria to be fulfilled by the treatment plan.

For example, the constraint data include a lower dose prescription limit (e.g. 2 Gy, 3 Gy, 4.5 Gy, 5.1 Gy, 5.10 Gy, 12.15 Gy, 16.0 Gy, 16 Gy or else). The lower dose prescription limit for example specifies a minimum value of the sum of all simulated irradiation doses received by a first predetermined volumetric percentage (e.g. 75%, 80%, 90%, 91%, 95.5%, 99%, 99.9%, 100% or else) of a target when following the treatment plan.

For example, the constraint data include an upper dose prescription limit (e.g. 2 Gy, 3 Gy, 4.5 Gy, 5.1 Gy, 5.10 Gy, 12.15 Gy, 16.0 Gy, 16 Gy, 20Gy, 25Gy or else). The upper dose prescription limit for example specifies a minimum value of the sum of all simulated irradiation doses received by a second predetermined volumetric percentage (e.g. 0%, 0.001%, 0.01%, 0.1%, 0.5%, 1%, 2%, 5%, 5.0%, 5.1%, 5.31%, 10% or else) of a target when following the treatment plan.

For example, the constraint data include an average dose prescription limit. For example, the average dose prescription limit may specify a maximum value of the average of all simulated irradiation doses received by a third predetermined volumetric percentage (e.g. equal to the first or the third predetermined volumetric percentage) of a target when following the treatment plan.

For example, the constraint data describes at least two of the lower, the upper and the average dose prescription limit. The lower and/or upper and/or average dose prescription limit is for example target-specific. The lower and/or upper and/or average dose prescription limit is for example the same for all of the at least one target. For example, a lower dose and/or upper and/or average prescription limit is only set for some of the targets. The lower and/or upper dose prescription limit may be referred to as minimum irradiation dose received by a certain volumetric percentage of a certain target when the treatment plan is performed. For example, the lower dose prescription limit may be described in other words as "when following the treatment plan, 95 Vol.-% of target A have to be irradiated with 16 Gy or more". For example, the upper dose prescription limit may be described in other words as "when following the treatment plan, 1 Vol.-% of target A have to be irradiated with 20 Gy or more".

In a (for example tenth) exemplary step, risk structure data is acquired. The risk structure data for example designates at least one of the one or more anatomical body parts as at least one risk structure for irradiation. The risk structure data for example designates at least one of the one or more anatomical body parts, which are not designated as a target, as at least one risk structure for irradiation. The risk structure data for example specifies at least one of the one or more anatomical body parts, which are not designated as a target by the target data, as at least one risk structure for irradiation. For example, an anatomical body part may not be designated as a target and also specified as a risk structure. For example, the risk structure data is determined based on a user input and based on the patient image data. For example, the risk structure data is linked to the patient image data. For example, the risk structure data and the patient image data use the same reference system (the first reference system).

For example, the risk structure data indicates a geometry (shape and/or position) of the at least one risk structure, for example in the first reference system. For example, the risk structure data indicates a geometry in the patient image data which is specified as the at least one risk structure for irradiation. The risk structure data for example specifies a first group of at least one of the one or more anatomical body parts as a first risk structure, a second group of the at least one of the one or more anatomical body parts as a second risk structure and so on. For example, different risk structures comprise different anatomical body parts. For example, each of the one or more anatomical body parts is only comprised in a single risk structure. For example, the risk structure dose data is determined for the at least one risk structure, for example for all of the at least one risk structure.

The constraint data for example describes at least one risk structure dose limit specifying a simulated irradiation dose received by the at least one risk structure. For example, the risk structure dose limit specifies a maximum value (e.g. 2 Gy, 3 Gy, 4.5 Gy, 5.1 Gy, 5.10 Gy, 12.15 Gy, 16.0 Gy, 16 Gy, 20Gy, 25Gy or else) of the sum of all simulated irradiation doses received by a first predetermined volumetric percentage (e.g. 0%, 0.001%, 0.01%, 0.1%, 0.5%, 1%, 2%, 5%, 5.0%, 5.1%, 5.31%, 10%, 50%, 75%, 80%, 90%, 91%, 95.5%, 99%, 99.9%, 100% or else) of a risk structure when following the treatment plan. The risk structure dose limit may specify other values. For example, the risk structure dose data may specify a maximum value of the average of all simulated irradiation doses received by the first predetermined volumetric percentage of the risk structure when following the treatment plan. The constraint data may describe different risk structure dose limits for different risk structures. The constraint data may describe the same risk structure dose limit for all risk structures.

In a (for example eleventh) exemplary step, the treatment plan is determined. The treatment plan is for example determined based on the irradiation data. The irradiation data is for example linked to the other data such as for example the beam shaping device data, the auxiliary outline data, the margin data, the position data and/or the target data.

The irradiation data is for example determined based on the irradiation data and the constraint data.

For example, total irradiation dose data is determined (for example after acquiring the constraint data) based on the treatment plan and the irradiation data, the total irradiation dose data describing the sum of all simulated irradiation doses received by (one or more of/all of) the voxels of (generated from) the patient image data (e.g. the voxels of a target) when following the treatment plan. For example, total irradiation dose data describes the sum of all simulated irradiation doses for each of the voxels individually. For example, the total irradiation dose data describes the sum of all simulated irradiation doses for each of paths of the treatment plan individually. For example, simulated irradiation doses received by the voxels of the patient image data when following the treatment plan are determined based on the irradiation data of all control points specifying the one or more paths of the treatment plan, based on the configurations of the beam shaping device at the control points and based on the (number of) monitor units to be emitted by the beam source at the control points (during movement of the irradiation direction and/or the support device, i.e. during movement along the one or more paths which are specified by the control points). For example, it is simulated how much irradiation would hit the individual voxels for a given control point, beam shaping device configuration and (number of) monitor unit(s). This simulation is for example performed for all control points of the treatment plan (with the corresponding beam shaping device configurations and the corresponding (number of) monitor units of the treatment plan). The sum of these simulated irradiations for individual voxels over all control points is for example described by the total irradiation dose data. The sum of all simulated irradiation doses is for example determined for each voxel of (obtained from) the patient image individually and/or for each voxel of a target (or of all targets) individually. The total irradiation data can be used to determine whether the treatment plan fits the criteria to be fulfilled by the treatment plan described by the constraint data. Additional constraints are possible such as a low normal tissue dose (gradient index) and/or a predetermined risk structure dose (e.g. maximum irradiation dose to be received by a risk structure) and/or a low sum of all arc weights (sum of all (numbers of) monitor units of all arcs).

The treatment plan is for example determined for combinations of margins, arc weights and blockings. In this context, an arc weight is for example defined as the sum of all (numbers of) monitor units to be emitted by the beam source during movement along one of the one or more paths. An arc weight is in this example specified for each of the one or more paths individually based on the control points of the individual path and based on the (number of) monitor units to be emitted at these control points. As noted above, the (number of) monitor units to be emitted at control points of a single path are for example identical. The arc weight in this case depends for example linearly on the number of control points. A blocking is for example defined as a configuration of the beam shaping device preventing irradiation to an irradiation area (at least one irradiation area) at a control point. A blocking is for example defined as a configuration of the beam source preventing irradiation to an irradiation area (at least one irradiation are) at a control point.

The treatment plan is for example determined only for combinations of margins, arc weights and blockings. This means that for example other possible parameters (e.g. control of individual collimator leaves independent from (auxiliary) outlines and/or blockings) are not taken into account for determining the treatment plan. For example, the (number of) monitor units to be emitted at the control points of each path are restricted as being identical for all control points within a path. For example, other possible parameters are regarded as being fixed (e.g. having a constant value) for all control points.

In a further exemplary step of the method according to the first aspect, path data is acquired. The path data for example describes one or more paths specified by one or more control points. The one or more control points for example are one or more of the at least one position of the patient support device in relation to the irradiation direction described by the position data. For example, the one or more paths specified by the treatment plan are the one or more paths described by the path data.

The path data for example further describes the one or more paths for several targets individually. For example, the path data further describes which of the at least one target shall be irradiated when moving along each path. For example, the path data describes a first path from which only a first target shall be irradiated and/or a second path from which only a second target different from the first target shall be irradiated and/or a third path from which both the first and the second target shall be irradiated. For example, the determination of the target projection data is performed for the one or more paths only for the targets which shall be irradiated from the one or more paths. For example, in case the path data describes a first path from which only a first target shall be irradiated, the target projection data is determined to only describe the outlines of the first target for the control points specifying the first path. For example, in case the path data describes a second path from which only a second target shall be irradiated, the target projection data is determined to only describe the outlines of the second target for the control points specifying the second path. For example, in case the path data describes a third path from which both a first and a second target shall be irradiated, the target projection data is determined to describe the outlines of the first target and the outlines of the second target for the control points specifying the third path.

The path data is for example determined as described in WO 2013/075743 A1 and/or WO 2015/039903 A1. For example, the path data is determined in another way. For example, the path data is specified by a user.

In a further exemplary step of the method according to the first aspect, blocking data is acquired. The blocking data for example describes blockings for the one or more paths specified by the treatment plan. As noted above, a blocking is for example defined as a configuration of the beam shaping device preventing irradiation to an irradiation area at a control point. The blocking data for example describes configurations of the beam shaping device preventing irradiation to an irradiation area at more than one control point. For example, the blocking data is determined based on the path data and the risk structure data. In this example, the blocking data may be determined so that a risk structure is not irradiated at more than a predetermined number (e.g. 0, 1, 2, 3 . . . ) of the control points of the one or more paths describes by the path data. The blocking data is for example determined using a stochastic and/or a gradient and/or a heuristic approach. This for examples ensures that the risk structures receive a low dose of irradiation. For example, in case of a blocking at a given control point, the target which lies in the blocked irradiation area (the irradiation area to which the irradiation is prevented by the blocking) is not irradiated. This for example reduces the irradiation dose received by this target, which reduction is for example compensated by irradiating the target from another control point, for example using a higher (number of) monitor unit(s).

The blocking data is for example determined as described in WO 2013/075743 A1 and/or WO 2015/039903 A1. For example, the blocking data is determined in another way. For example, the blocking data is specified by a user.

In a further exemplary step of the method according to the first aspect, a plurality of auxiliary treatment plans is generated. For example, the auxiliary treatment plans comprised in the plurality of auxiliary treatment plans differ from one another only in the combinations of margins, arc weights and blockings. For example, the plurality of auxiliary treatment plans consists of several auxiliary treatment plans, wherein each of the several auxiliary treatment plans has a different combination of margins, arc weights and blockings. For example, all parameters independent from the margins, arc weights and blockings are the same for all auxiliary treatment plans. For example, all parameters other than the margins, arc weights and blockings are the same for all auxiliary treatment plans. The plurality of auxiliary treatment plans are for example generated based on the constraint data. For example, at least some of the auxiliary treatment plans are generated using random configurations of the margins, arc weights and/or blockings, using a configuration of margins, arc weights and/or blockings specified by a user or else. For example, one auxiliary treatment plan is generated using a margin equal to zero and no blockings and arc-weights such that all of the at least one target receive a simulated irradiation dose which fulfills the lower and/or upper dose prescription limit. Additional auxiliary treatment plans are for example generated based on the one auxiliary treatment plan, wherein for each of the additional auxiliary treatment plans, at least one of the margins, arc-weights and blockings is changed (e.g. randomly and/or heuristically and/or using a gradient-based approach).

In a further exemplary step of the method according to the first aspect, target dose data is determined based on the irradiation data. The target dose data for example depends on the control points specifying the one or more paths of the auxiliary treatment plan. For example, the one or more paths are identical for all auxiliary treatment plans. In this case, for example the control points are identical for all auxiliary treatment plans. The target dose data is for example determined for one or more of the auxiliary treatment plans, for example for all auxiliary treatment plans. For example, the target dose data is determined for one or more of the at least one target, for example for all of the at least one target. The target dose data for example describes the sum of all simulated irradiation doses received by the at least one target when following the auxiliary treatment plan. For example, in case of more than one target, the target dose data describes a sum of all simulated irradiation doses for each of the targets individually.

For example, the target dose data is determined in a way similar to the total irradiation dose data except that the target dose data is only determined for voxels comprised in (one or more of/all of) the at least one targets. For example, the target dose data describes the sum of all simulated irradiation doses received by (one or more of/all of) the voxels of (generated from) the patient image data comprised in (one or more of/all of) the at least one targets when following the auxiliary treatment plan. For example, the target dose data describes the sum of all simulated irradiation doses for each of the voxels of the target(s) individually. For example, simulated irradiation doses received by the voxels of the patient image data when following the auxiliary treatment plan are determined based on the irradiation data of all control points specifying the one or more paths of the auxiliary treatment plan, based on the configurations of the beam shaping device at the control points and based on the (number of) monitor units to be emitted by the beam source at the control points (during movement of the irradiation direction and/or the support device, i.e. during movement along the one or more paths which are specified by the control points). For example, it is simulated how much irradiation would hit the individual voxels for a given control point, beam shaping device configuration and (number of) monitor unit(s). This simulation is for example performed for all control points of the auxiliary treatment plan (with the corresponding beam shaping device configurations and the corresponding (number of) monitor units of the treatment plan). The sum of these simulated irradiations for individual voxels comprised in the target(s) over all control points is for example described by the target dose data. The sum of all simulated irradiation doses is for example determined for each voxel of (obtained from) the patient image and comprised in the target(s) individually.

In a further exemplary step of the method according to the first aspect, rating data is determined at least based on the target dose data and the constraint data. The rating data is for example determined based on additional data as will be described below. The rating data is determined for one or more of the auxiliary treatment plans, for example for all auxiliary treatment plans. The rating data for example describes a degree to which the auxiliary treatment plan(s) match(es) the criteria to be fulfilled by the treatment plan. For example, the rating data assigns one or more numerical values to each of the plurality of auxiliary treatment plans, wherein the one or more numerical values for example indicate how well a given auxiliary treatment plan matches the criteria to be fulfilled by the treatment plan.

In a further exemplary step of the method according to the first aspect, one of the plurality of auxiliary treatment plans is selected as the treatment plan based on the rating data. For example, the plurality of auxiliary treatment plans are ranked based on the rating data and the auxiliary treatment plan which has the highest ranking is selected. The selection is for example performed using heuristic and/or stochastic and/or gradient-based exploration.

In a further exemplary step of the method according to the first aspect, normal tissue dose data is determined. This step is for example performed for one or more (for example for each) of the plurality of auxiliary treatment plans after having determined the target dose data. The normal tissue dose data is for example determined based on the irradiation data. For example, the normal tissue dose data describes the sum of all simulated irradiation doses received by normal tissue when following the auxiliary treatment plan. For example, the normal tissue dose data is determined for several (e.g. all) voxels of the patient image data individually. For example, the normal tissue dose data is determined for several (e.g. all) voxels of normal tissue of the patient individually. For example, the normal tissue includes all of the one or more anatomical body parts of the patient described by the patient image data. For example, the normal tissue includes all of the one or more anatomical body parts of the patient described by the patient image data which are not designated as a target (and/or a risk structure).

For example, the normal tissue dose data is determined in a way similar to the total irradiation dose data except that the normal tissue dose data is determined for voxels comprised in normal tissue. For example, the normal tissue dose data describes the sum of all simulated irradiation doses received by (one or more of/all of) the voxels of (generated from) the patient image data comprised in the normal tissue when following the auxiliary treatment plan. For example, the normal tissue dose data describes the sum of all simulated irradiation doses for each of the voxels of the normal tissue individually. For example, simulated irradiation doses received by the voxels of the patient image data when following the auxiliary treatment plan are determined based on the irradiation data of all control points specifying the one or more paths of the auxiliary treatment plan, based on the configurations of the beam shaping device at the control points and based on the (number of) monitor units to be emitted by the beam source at the control points (during movement of the irradiation direction and/or the support device, i.e. during movement along the one or more paths which are specified by the control points). For example, it is simulated how much irradiation would hit the individual voxels for a given control point, beam shaping device configuration and (number of) monitor unit(s). This simulation is for example performed for all control points of the auxiliary treatment plan (with the corresponding beam shaping device configurations and the corresponding (number of) monitor units of the treatment plan). The sum of these simulated irradiations for individual voxels comprised in the normal tissue over all control points is for example described by the normal tissue dose data. The sum of all simulated irradiation doses is for example determined for each voxel of (obtained from) the patient image and comprised in the normal tissue individually.

For example, the rating data is determined furthermore based on the normal tissue dose data.

In a further exemplary step of the method according to the first aspect, risk structure dose data is determined. This step is for example performed for one or more (for example for each) of the plurality of auxiliary treatment plans, for example before determining the rating data. For example, the risk structure dose data is determined based on the irradiation data and the risk structure data. The risk structure data is for example acquired before determining the risk structure dose data as noted above. The risk structure dose data is for example determined for one or more of the at least one risk structure, for example for all of the at least one risk structure. The risk structure dose data for example describes the sum of all simulated irradiation doses received by (one or more of or all of) the at least one risk structure when following the auxiliary treatment plan.

For example, the risk structure dose data is determined in a way similar to the total irradiation dose data except that the risk structure dose data is only determined for voxels comprised in the risk structure(s). For example, risk structure dose data describes the sum of all simulated irradiation doses received by (one or more of/all of) the voxels of (generated from) the patient image data comprised in the risk structure(s) when following the auxiliary treatment plan. For example, the risk structure dose data describes the sum of all simulated irradiation doses for each of the voxels of a (or all) risk structure(s) individually. For example, simulated irradiation doses received by the voxels of the patient image data when following the auxiliary treatment plan are determined based on the irradiation data of all control points specifying the one or more paths of the auxiliary treatment plan, based on the configurations of the beam shaping device at the control points and based on the (number of) monitor units to be emitted by the beam source at the control points (during movement of the irradiation direction and/or the support device, i.e. during movement along the one or more paths which are specified by the control points). For example, it is simulated how much irradiation would hit the individual voxels for a given control point, beam shaping device configuration and (number of) monitor unit(s). This simulation is for example performed for all control points of the auxiliary treatment plan (with the corresponding beam shaping device configurations and the corresponding (number of) monitor units of the treatment plan). The sum of these simulated irradiations for individual voxels comprised in a risk structure over all control points is for example described by the risk structure dose data. The sum of all simulated irradiation doses is for example determined for each voxel of (obtained from) the patient image and comprised in a risk structure individually.

For example, the rating data is determined furthermore based on the risk structure dose data.

In a further exemplary step of the method according to the first aspect, first difference data is determined. This step is for example performed for one or more (for example for each) of the plurality of auxiliary treatment plans, for example after determining (after having determined) the target dose data and for example before determining the rating data. For example, the first difference data is determined based on the constraint data and the target dose data. For example, the first difference data is determined for the at least one target, for example for all of the at least one target, for example for each of the at least one target individually. For example, the first difference data describes a first difference between the lower dose prescription limit and the sum of all simulated irradiation doses received by the at least one target when following the auxiliary treatment plan.

In a further exemplary step of the method according to the first aspect, second difference data is determined. This step is for example performed for one or more (for example for each) of the plurality of auxiliary treatment plans, for example after determining (after having determined) the target dose data and for example before determining the rating data. For example, the second difference data is determined based on the constraint data and the target dose data. For example, the second difference data is determined for the at least one target, for example for all of the at least one target, for example for each of the at least one target individually. For example, the second difference data describes a second difference between the upper dose description limit and the sum of all simulated irradiation doses received by the at least one target when following the auxiliary treatment plan.

In a further exemplary step of the method according to the first aspect, total arc weight data is determined. This step is for example performed for one or more (for example for each) of the plurality of auxiliary treatment plans and for example before determining the rating data. For example, the total arc weight data is determined based on the (number of) monitor units to be emitted by the beam source during movement along the one or more paths specified by the auxiliary treatment plan. For example, the total arc weight data describes a sum of all arc weights of all paths specified by the auxiliary treatment plan.

For example, the degree to which the auxiliary treatment plan matches the criteria to be fulfilled by the treatment plan (the degree being described by the rating data) is specified at least by the first difference described by the first difference data, the second difference described by the second difference data and/or the sum of all arc weights described by the total arc weight data.

In a further exemplary step of the method according to the first aspect, gradient index data is determined. This step is for example performed for one or more (for example for each) of the plurality of auxiliary treatment plans, for example after determining (after having determined) the normal tissue dose data and for example before determining the rating data. For example, the gradient index data is determined based on the normal tissue dose data. For example, the gradient index data describes a relation between a first volume and a second volume. For example, the first volume is a value describing the amount of volume of the normal tissue which receives at least a first predetermined sum of all simulated irradiation doses when following the auxiliary treatment plan. For example, the second volume is a value describing the amount of volume of the normal tissue which receives at least a second predetermined sum of all simulated irradiation doses when following the auxiliary treatment plan. For example, the first predetermined sum may be 10 Gy, the second predetermined sum may be 20 Gy, the first volume may be 120 mm$^3$ and the second volume may be 20 mm$^3$. Of course, other values are possible depending for example on the patient image data, the auxiliary treatment plan and the first and second predetermined sum.

The first and/or second predetermined sum may be described by the constraint data. The first and/or second predetermined sum may be described by other data which is acquired. The first and/or second predetermined sum may be determined based on another constraint described by the constraint data, for example based on the upper or lower prescription dose limit of a target. For example, the first predetermined sum may be determined as 50% of the lower prescription limit and the second predetermined sum may be determined as 100% of the lower prescription limit. For example, the first predetermined sum may be determined as 50% of the upper prescription limit and the second predetermined sum may be determined as 100% of the upper prescription limit. In this example, other percentages are possible as long as the second sum is higher than the first sum. For example, if the second sum is lower than the first sum, the inverse gradient index is used instead of the gradient index to determine the relation between the first and the second volume.

For example, the degree to which the auxiliary treatment plan matches the criteria to be fulfilled by the treatment plan (the degree being described by the rating data) is specified (furthermore) by the relation between the first volume and the second volume described by the gradient index data. In the above example, this relation between the first volume and the second volume may be expressed as 20 mm$^3$/120 mm$^3$ or as ⅙. For example, a relation (a gradient index) close to 1 is regarded as a good result of the auxiliary treatment plan. The gradient index data is for example determined describing a value of a gradient index, wherein the gradient index is for example determined as described in *A simple dose gradient measurement tool to complement the conformity index* (Ian Paddick, M. Sc., and Bodo Lippitz, M. D., in J Neurosurg (Suppl) 105:194-201, 2006.

In a further exemplary step of the method according to the first aspect, third difference data is determined. This step is for example performed for one or more (for example for each) of the plurality of auxiliary treatment plans, for example after determining (after having determined) the risk structure dose data and for example before determining the rating data. For example, the third difference data is determined based on the constraint data and the risk structure dose data. For example, the third difference data is determined for the at least one target, for example for all of the at least one target, for example for each of the at least one target individually. For example, the third difference data is determined for the at least one risk structure, for example for all of the at least one risk structure, for example for each of the at least one risk structure individually. For example, the third difference data describes a third difference between the at least one risk structure dose limit and the sum of all simulated irradiation doses received by the at least one risk structure when following the auxiliary treatment plan. For example, the degree to which the auxiliary treatment plan matches the criteria to be fulfilled by the treatment plan (the degree being described by the rating data) is specified furthermore by the third difference described by the third difference data.

After the selection of one of the plurality of auxiliary treatment plans, the method for example continues with a step of generating a plurality of secondary auxiliary treatment plans. This generation and a subsequent selection of one of the secondary auxiliary treatment plans is for example performed using heuristic, stochastic and/or gradient-based exploration. For example, multiple iterations of generating (secondary, tertiary, quaternary . . . ) auxiliary treatment plans and subsequently selecting one of these auxiliary treatment plans are performed using heuristic, stochastic and/or gradient-based exploration. For example, one or more optimization algorithms are used to finally select one of the (secondary, tertiary, quaternary . . . ) auxiliary treatment plans as the treatment plan. A detailed example will be described in the description of embodiments.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a medical system, comprising:
  the at least one computer (2) according to the fourth aspect;

at least one electronic data storage device (3) storing at least the patient image data; and a medical device (4) for carrying out a medical procedure on the patient, wherein the at least one computer is operably coupled to the at least one electronic data storage device for acquiring, from the at least one data storage device, at least the patient image data, and the medical device for issuing a control signal to the medical device for controlling the operation of the medical device on the basis of the treatment plan.

In an example of the system according to the fifth aspect, the medical device comprises a radiation treatment apparatus comprising a treatment beam source, a beam shaping device and a patient support device, wherein the at least one computer is operably coupled to the radiation treatment apparatus for issuing a control signal to the radiation treatment apparatus for controlling, on the basis of the treatment plan, at least one of the operation of the treatment beam source,
the operation of the beam shaping device or
the position of the patient support device.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of performing treatment of a patient, for example using radiotherapy and/or radiosurgery. More particularly, the invention does not involve or in particular comprise or encompass any surgical or therapeutic activity (radiotherapeutic/radiosurgical step). The invention is instead directed as applicable to determining a treatment plan. For this reason alone, no surgical or therapeutic activity and in particular no surgical or therapeutic step is necessitated or implied by carrying out the invention.

The present invention also relates to the use of the device/system or any embodiment thereof for determining a treatment plan. For example, the treatment plan specifies all necessary parameters which are used to control a treatment device/system, for example comprising a radiotherapy and/or radiosurgery treatment device/system. The determined treatment plan may be used as a plan for treating a patient using radiotherapy and/or radiosurgery which use is only possible after having determined the treatment plan. The use comprises for example at least one of the following steps: acquiring patient image data (e.g. inputting by a user), acquiring target data (e.g. designating by a user, based on the patient image data), acquiring position data, determining target projection data, acquiring margin data, determining auxiliary outline data, determining beam shaping device data, determining irradiation data, acquiring constraint data and determining the treatment plan. The use of the device/system of any embodiment thereof for determining a treatment plan may comprise steps of user input such as a specification of one or more constraints described by the constraint data, specification of one or more targets, specification of one or more risk structures and specification of one or more thresholds mentioned in this application (e.g. optimization algorithm conversion threshold and/or thresholds t1 to t7). The use may comprise selecting at least one of the aforementioned parameters from a given list which is for example provided to the user. The use may comprise using a graphical user interface (GUI) for the user input and/or the output of data representing the determined treatment plan. For example, data representing the (determined/selected) treatment plan is output on a display device.

Definitions

In this section, definitions for specific terminology used in this disclosure are offered which also form part of the present disclosure.

Data

In the following, a summary of data mentioned in this application will be given. The below summary is not to be interpreted as the only possible definitions. The data are defined in the general description of the invention in detail.

Patient image data for example describes one or more anatomical body parts of a patient.

Target data for example specifies an anatomical body part as target for irradiation.

Position data for example describes control points (e.g. relative positions between the patient support device in relation to the irradiation direction).

Target projection data for example describes an outline of the target projected into the beam's-eye-view.

Margin data for example specifies numerical values of margins (e.g. −0.5 mm, 0 mm, 0.5 mm, 1 mm).

Auxiliary outline data for example describes the outline of the target including a margin.

Beam shaping device data for example describes a shape of the collimator for a given outline (e.g. an outline including a margin).

Irradiation data for example describes the simulated irradiation dose received by a voxel of the patient image for a given collimator shape and control point.

Constraint data for example describes a lower prescription dose limit, an upper prescription dose limit and a risk structure dose limit.

Path data for example describes movement directions for one or more arcs using control points.

Blocking data for example describes blockings for one or more arcs, preventing irradiation of a target at given control points.

Rating data for example describes a degree to which the auxiliary treatment plan matches the criteria to be fulfilled by the treatment plan (e.g. ranking of auxiliary treatment plans with different configurations of margins, arc weights and blockings).

Total irradiation dose data for example describes the simulated irradiation dose received by a voxel of the patient image for a given treatment plan (e.g. equal to the sum of all irradiation doses described by the irradiation data of the treatment plan).

Target dose data for example describes the sum of all simulated irradiation doses received by the at least one target when following the (auxiliary) treatment plan (simulated target dose).

First difference data for example describes the difference between the lower dose prescription limit and the simulated target dose.

Second difference data for example describes the difference between the upper dose prescription limit and the simulated target dose.

Total arc weight data for example describes the sum of all arc weights of all paths specified by the (auxiliary) treatment plan.

Normal tissue dose data for example describes the sum of all simulated irradiation doses received by normal tissue when following the (auxiliary) treatment plan.

Gradient index data for example describes the gradient index.

Risk structure data for example designates an anatomical body part of the patient as a risk structure for irradiation.

Risk structure dose data for example describes the sum of all simulated irradiation doses received by the at least one risk structure when following the auxiliary treatment plan (simulated risk structure dose).

Third difference data for example describes the difference between the risk structure dose limit and the simulated risk structure dose.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (World Wide Web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "targets". The present invention relates to the field of medicine and for example to the use of beams, such as radiation beams, to treat parts of a patient's body, which are therefore also referred to as treatment beams. A treatment beam treats body parts which are to be treated and which are referred to in the following as "targets". These body parts are for example parts of a patient's body, i.e. anatomical body parts. An anatomical body parts is for example a part of an organ of the patient or a complete organ of a patient. An anatomical body part for example comprises parts of one or more organs of a patient. Ionizing radiation (irradiation) is for example used for the purpose of treatment. For example, the treatment beam (irradiation beam, beam emitted by a beam source, irradiation emitted by the beam source after having passed a beam shaping device) comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part.

The treatment beam is preferably controlled such that it passes through the target. However, the treatment beam can have a negative effect on body parts outside the treatment body part (risk structures and (parts of) normal tissue). These body parts are referred to here as "outside body parts". Generally, a treatment beam has to pass through outside body parts in order to reach and so pass through the treatment body part.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Registering

The n-dimensional image of a body is registered when the spatial location of each point of an actual object within a space, for example a body part in an operating theatre, is assigned an image data point of an image (CT, MR, etc.), the image for example being stored in a memory of a computer or of a navigation system.

Image Registration

Image registration (sometimes referred to only as "registration") is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
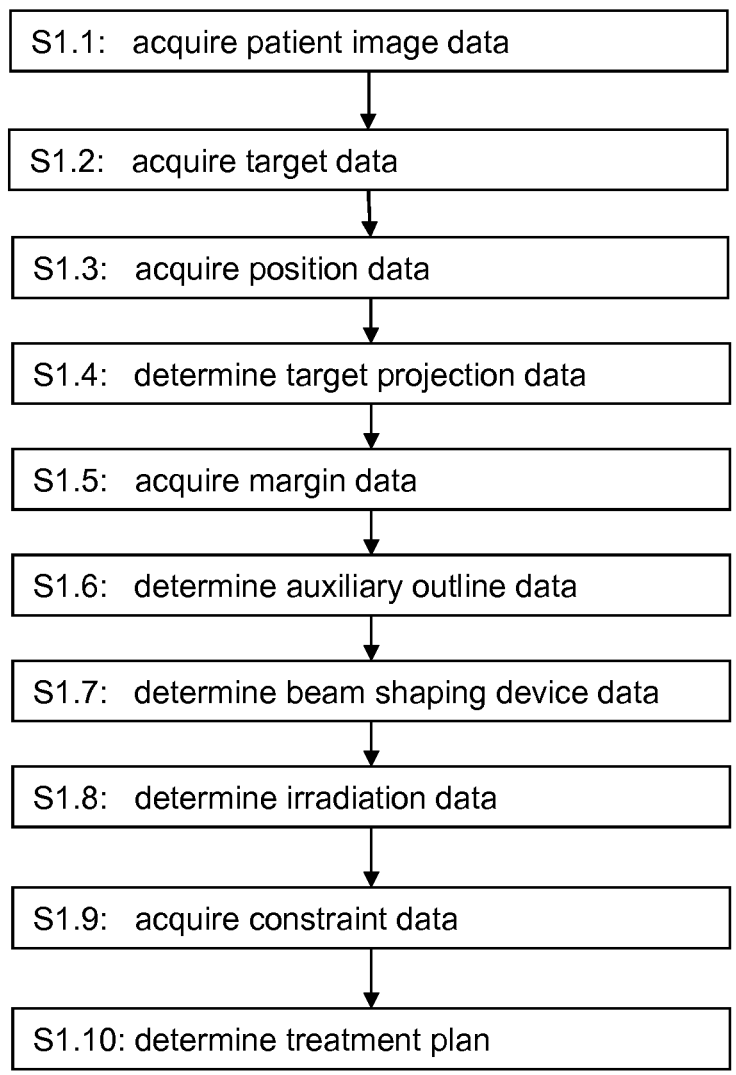
FIG. 1 illustrates the basic steps of the method according to a first aspect.

FIG. 1 illustrates the basic steps of the method according to the first aspect, in which step S1.1 encompasses acquiring patient image data, step S1.2 encompasses acquiring target data, S1.3 encompasses acquiring position data, S1.4 encompasses determining target projection data, S1.5 encompasses acquiring margin data, S1.6 encompasses determining auxiliary outline data, S1.7 encompasses determining beam shaping device data, S1.8 encompasses determining irradiation data, S1.9 encompasses acquiring constraint data and S1.10 encompasses determining the treatment plan.

Figure 2:
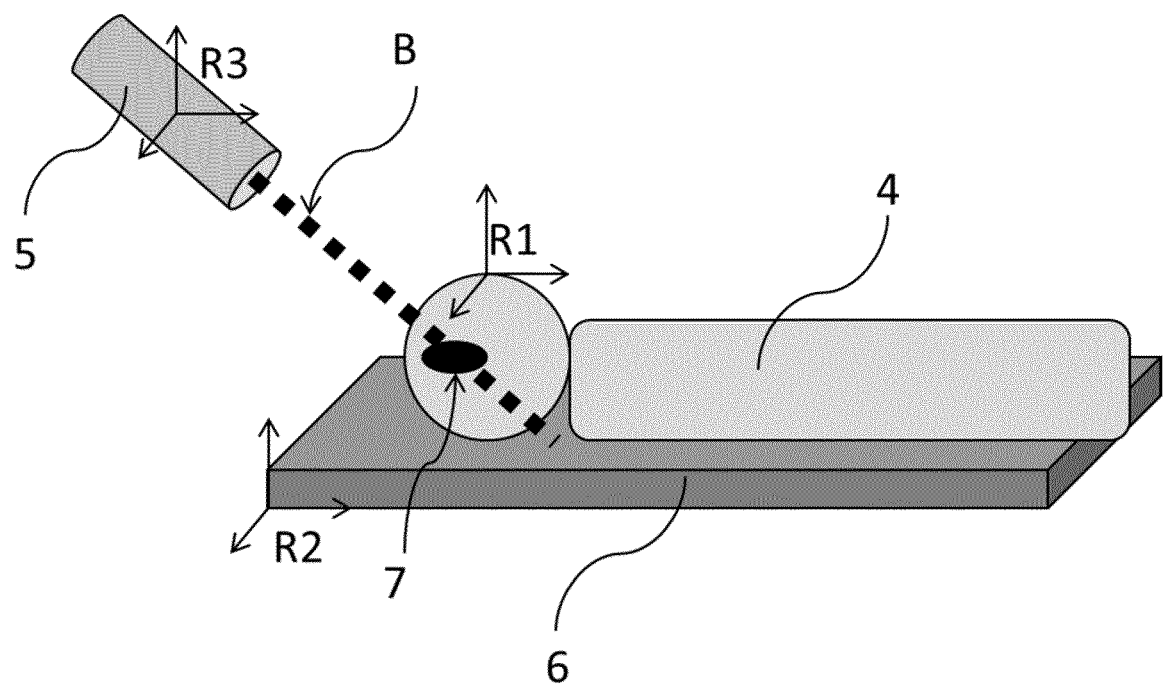
FIG. 2 shows a schematic illustration of the system according to the fifth aspect.

FIG. 2 shows a schematic illustration of the system according to the fifth aspect. The beam shaping device 5 may emit an irradiation beam B. The irradiation beam B may be a simulated irradiation beam when conducting the method for determining the treatment plan. A patient 4 may be positioned on the patient support device 6. The patient may be in a position defined in a first reference system R1, the patient support device may be in a position defined by a second reference system R2 and the irradiation direction may be defined by a third reference system R3. The patient image data may also be defined in the first reference system R1, for example by registering the patient to the patient image data using a commonly known image registration method. The irradiation beam B may irradiate a target 7 which is an anatomical body part of the patient 4 and in the shown example located in the head of the patient (e.g. a brain tumor). The beam shaping device 5 may be movable around the patient support device 6. The patient support device 6 itself may also be movable. Transformations between R1, R2 and R3 are for example known. These transformations may be predetermined, determined using image registration or optical tracking means, specified by a user or else. The irradiation direction may be equal to the position of the beam shaping device 5 in the third reference system.

Figure 3:
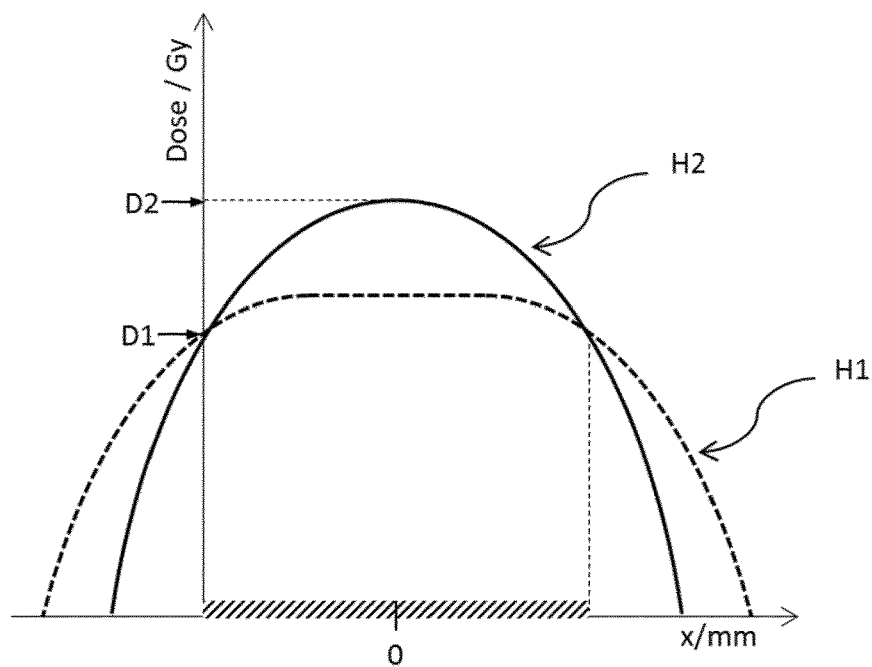
FIG. 3 shows spatial dose distributions.

FIG. 3 shows spatial dose distributions for two different beam shaping device configurations. The dose profiles for the two different beam shaping device configurations, for example corresponding to two different auxiliary outlines for two different margins of a given outline, are very different. To compare the profiles, they are both normalized to fulfill a minimum dose of D1. The spatial dose distributions are represented as 1D dose profiles. The primary (horizontal) axis denotes spatial position and the secondary (vertical) axis denotes a received irradiation dose at the respective spatial positions. The area of a target to be irradiated is indicated in the primary (horizontal) axis with a dashed bar. A first spatial dose distribution for a first configuration of the beam shaping device is shown as H1. A second spatial dose distribution for a second configuration of the beam shaping device is shown as H2. The minimum dose received by the target in the case of H1 and H2 is indicated by D1 (e.g. normalized as noted above). The maximum dose received by the target in the case of H2 is indicated by D2. It is clear that the maximum dose received by the target is higher for H2 than for H1, which means that the target receives a higher irradiation dose in the case of H2.

Furthermore, the areas outside the target region indicated by the dashed bar receive different amounts of irradiation depending on the configuration of the beam shaping device. In the case of H1, a larger area (volume) of tissue outside the target receives irradiation. Consequently, tissue which is not to be treated (outside the target) receives large irradiation doses according to H1. In this example, the gradient index of H2 is closer to a value of "1" than the gradient index of H1.

As noted above, the shape of the functions H1 and H2 (the spatial irradiation dose distribution) depends on the configuration of the beam shaping device. In the case of a collimator blocking parts of the irradiation emitted by the beam source, physical effects such as scattering of the irradiation have to be taken into account. Not only the shape of a mask through which irradiation passes determines the shape of the functions H1 and H2, but also the absolute dimensions of the mask. In general, the spatial irradiation dose distribution will look more like H1 in case a larger hole is used in the mask allowing for more irradiation to pass. The smaller the hole in the mask (e.g. a collimator), the more will the spatial irradiation dose distribution look like H2. The absolute dose values can be adjusted by increasing/decreasing the amount of irradiation emitted by the beam source, while the spatial irradiation dose distribution will not change (shape of the curve (e.g. H1 or H2) stays the same).

Figure 4:
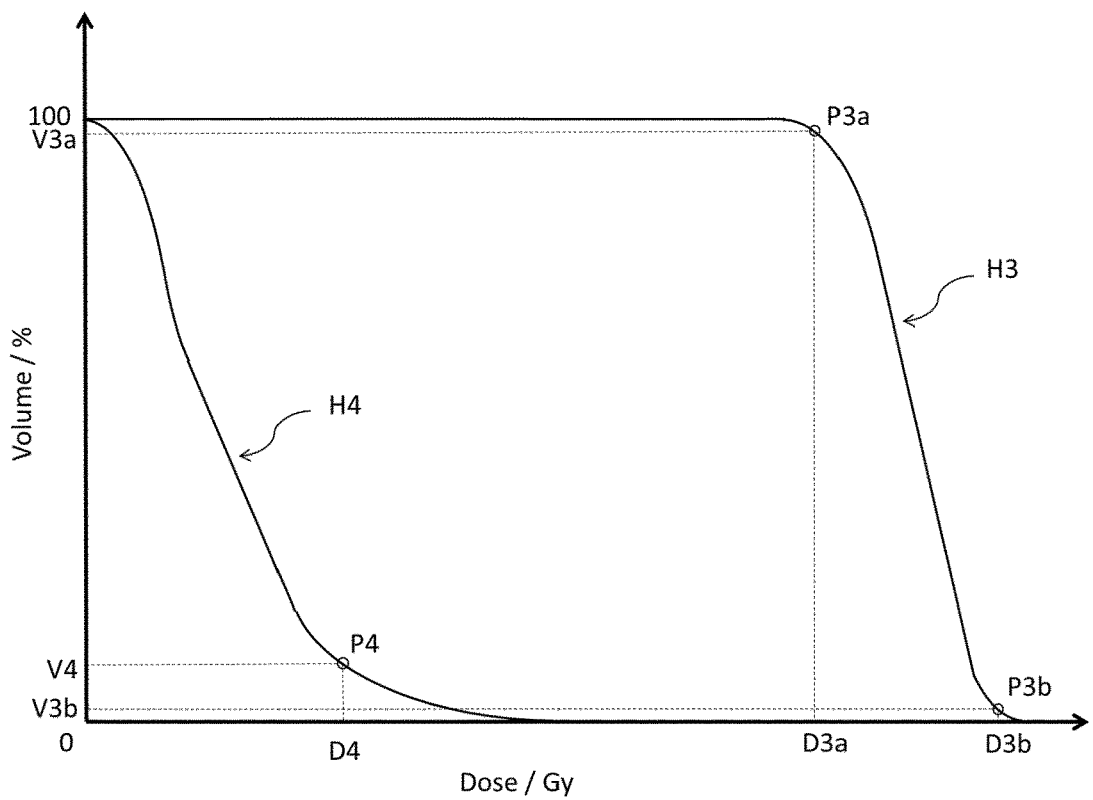
FIG. 4 shows a cumulative dose-volume histogram.

FIG. 4 shows a cumulative dose-volume histogram. The primary (horizontal) axis denotes an irradiation dose and the secondary (vertical) axis denotes a volumetric percentage (e.g. a volumetric percentage of a target or a volumetric percentage of all anatomic body parts described by the patient image data) of tissue which is to receive the respective irradiation dose.

For example, the curve H3 indicates a planned volumetric irradiation dose distribution for a given target. A lower prescription limit P3a is defined as a minimum amount D3a Gy to be received by V3a Vol.-% of the given target. For example, the lower prescription limit may define a minimum amount of 16 Gy to be received by 95 Vol.-% of the given target. An upper prescription limit P3b is defined as a minimum amount of D3b Gy received by V3b Vol.-% of the given target. For example, the upper prescription limit may define a minimum amount of 20 Gy to be received by 1 Vol.-% of the given target.

For example, the curve H4 indicates a planned irradiation dose for a risk structure. An irradiation dose limit P4 is defined as a maximum amount of D4 Gy to be received by V4 Vol.-% of the risk structure. For example, the irradiation dose limit may define a maximum amount of 5 Gy to be received by 10 Vol.-% of the risk structure, e.g. by the 10% of the risk structure which receive the highest irradiation dose. Instead of a risk structure, curve H4 may be defined for the normal tissue.

Both curves H3 and H4 may be influenced by a user, for example by defining one or more points through which the curves shall run (e.g. a lower dose prescription limit P3a and/or an upper dose prescription limit P3b). Note that the curves do not necessarily run through the points. For example, a user may specify a maximum dose limit to be received by a risk structure as P4. The curve H4 may run through the point P4, but may also lie below the point P4. That is, the points defined by the user restrict the curve at a given dose to be equal to or lower than a set value. The points defined by the user may alternatively restrict the curve at a given dose to be equal to or higher than a set value. The treatment plan may be determined based on this user input, i.e. a lower point prescription limit, an upper dose prescription limit, a normal tissue dose limit and/or a risk structure dose limit. A perfect treatment plan would result in an irradiation which perfectly fits all the constraints (boundary conditions) specified by the user (e.g. perfectly fits the lower and upper dose prescription limit specified as P3a and P3b). However, the determination of such a perfect treatment plan is very cumbersome—in some cases even impossible—and also may result in several disadvantages (longer treatment time, higher energy consumption, necessary patient re-alignment etc.). Therefore, a compromise between the given boundary conditions (constraints) and these disadvantages has to be found in order to determine the treatment plan.

As described above with respect to FIG. 1, patient image data is acquired, for example x-ray, ultrasonic, CT, MR or CBCT image data. Then, target data is acquired. For example, a user specifies the at least one target (the geometry (shape and position)) in the patient image data. Afterwards, position data is acquired. The position data describes several control points for several paths (arcs). For at least some of the control points (for example for all of the control points), projections of the at least one target (outlines) are determined. One example of a determined outline of a single target is shown as outline 2 in FIGS. 5 to 7.

Figure 6:
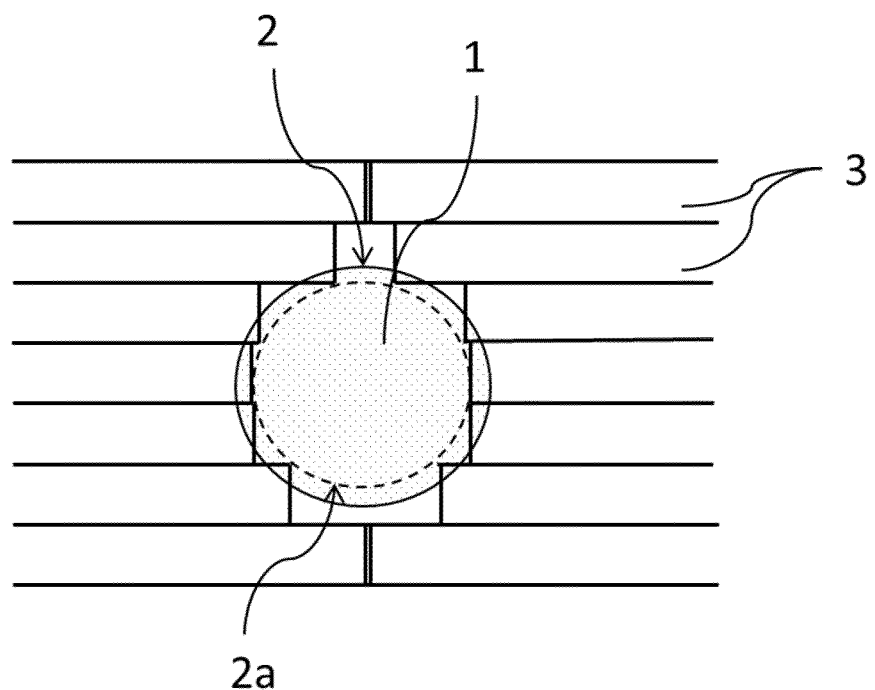
FIG. 6 shows a configuration of the beam shaping device for a given auxiliary outline.
Figure 7:
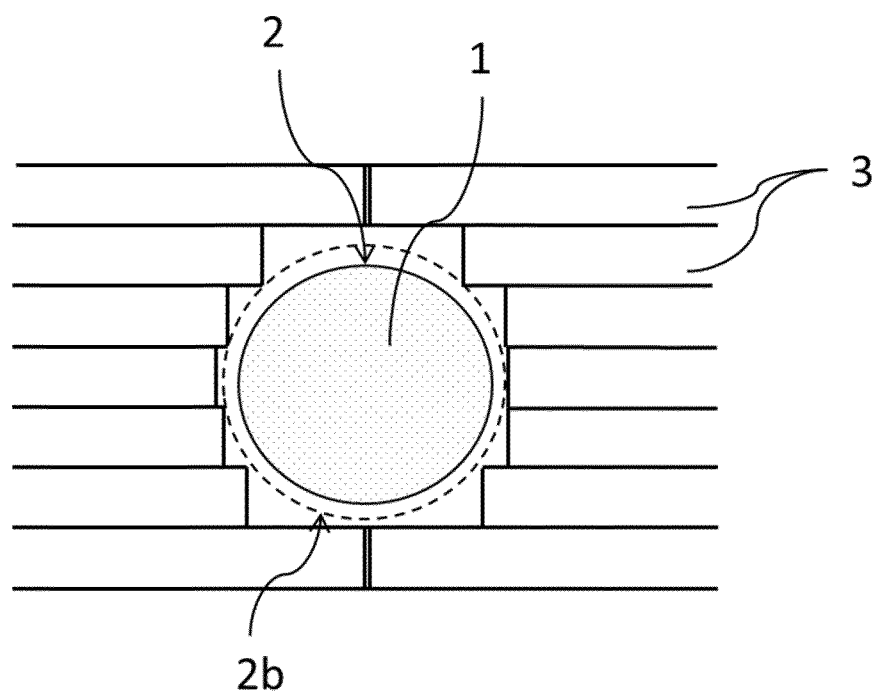
FIG. 7 shows a configuration of the beam shaping device for another given auxiliary outline.

Then, margin data is acquired. Based on the margins described by the margin data and the determined outlines, auxiliary outlines are determined. One example of an auxiliary outline correlated with the single target used for determining the outline 2 is shown as 2a and 2b in FIGS. 6 and 7. In FIG. 6, the auxiliary outline 2a lies within the outline 2 (is enclosed in the outline 2). In this case, a negative margin (e.g. −1 mm) was used to determine the auxiliary outline 2a from the outline 2. In FIG. 7, the auxiliary outline 2b encloses the outline 2. In this case, a positive margin (e.g. 0.5 mm) was used to determine the auxiliary outline 2b from the outline 2. As can be seen from both FIGS. 6 and 7, the auxiliary outlines 2a and 2b each have a homogeneous distance to the outline 2. These distances are each defined by the margin (e.g. −1 mm and 0.5 mm) used to generate the auxiliary outlines 2a and 2b, respectively. The auxiliary outline may be regarded as enlarged or scaled-up (using size and/or shape adjustment) in the case of FIG. 7 and as shrunk or scaled-down (using size and/or shape adjustment) in the case of FIG. 6.

After having determined the auxiliary outline data, the method proceeds with determining beam shaping device data. The beam shaping device data describes configurations of the beam shaping device which enable irradiation of one or more irradiation areas specified by the one or more auxiliary outlines.

Figure 5:
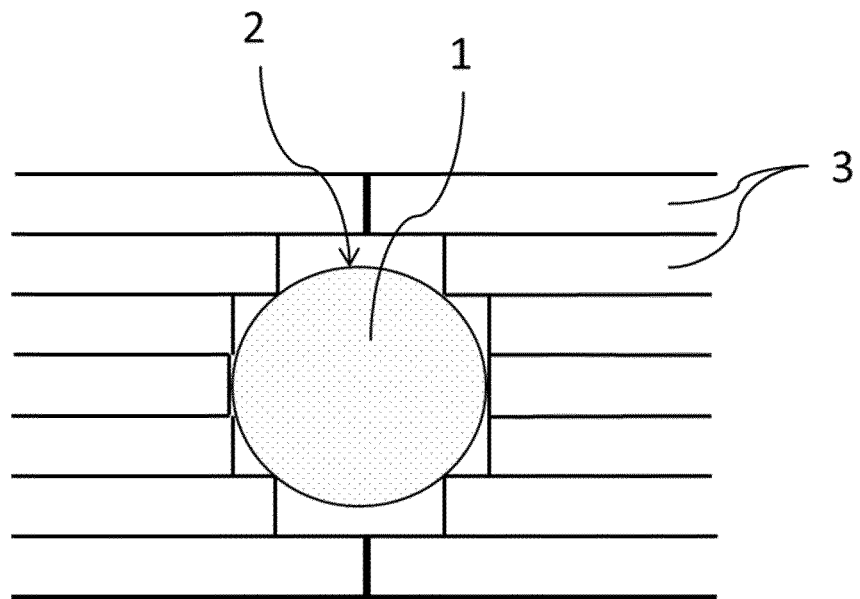
FIG. 5 shows a configuration of the beam shaping device for a given outline.

In FIGS. 5 to 7, the beam shaping device and the target are shown in a beam's-eye-view for a given control point. The projection of the target 1 into the plane perpendicular to the simulated beam direction (which here corresponds to the viewing direction) results in a two-dimensional shape of the target 1 indicated by a dotted area in FIGS. 5 to 7. In the example of FIGS. 5 to 7, a multi-leaf collimator is shown as the beam shaping device. It should be clear that other beam shaping devices are possible. In FIGS. 5 to 7, positions of collimator leaves 3 are specified by the configuration of the beam shaping device described by the beam shaping device data.

FIG. 5 shows a configuration of the beam shaping device for a given auxiliary outline determined from an outline 2 for a margin equal to zero. In this case, as noted above, the auxiliary outline is equal to the outline 2. In the example shown in FIG. 5, the collimator leaves do not cross the auxiliary outline which is equal to the outline 2. In particular, the collimator leaves are adapted to/fit to the auxiliary outline which is equas to the outline 2. The area through which irradiation can pass is defined by the collimator leaves. This area is minimized as much as possible whilst the collimator leaves do not cross the auxiliary outline.

FIG. 6 shows a configuration of the beam shaping device for a given auxiliary outline 2a determined from an outline 2 for a margin smaller than zero. In this case, as noted above, the auxiliary outline 2a lies inside the outline 2. In the example shown in FIG. 6, the collimator leaves cross the outline 2, but do not cross the auxiliary outline 2a. In particular, the collimator leaves are adapted to/fit to the auxiliary outline 2a. Also in this case, the area through which irradiation can pass is defined by the collimator leaves and minimized as much as possible whilst the collimator leaves do not cross the auxiliary outline 2a.

FIG. 7 shows a configuration of the beam shaping device for a given auxiliary outline 2b determined from an outline 2 for a margin larger than zero. In this case, as noted above, the auxiliary outline 2b encloses the outline 2. In the example shown in FIG. 7, the collimator leaves do not cross the outline 2 and also do not cross the auxiliary outline 2b. In particular, the collimator leaves are adapted to/fit to the auxiliary outline 2b. Also in this case, the area through which irradiation can pass is defined by the collimator leaves and minimized as much as possible whilst the collimator leaves do not cross the auxiliary outline 2a.

After having determined the beam shaping device data, the method proceeds with determining irradiation data for the configurations of the beam shaping device. Then, constraint data is acquired and the treatment plan is determined.

For example, a plurality of auxiliary treatment plans is determined. After the selection of one of the plurality of auxiliary treatment plans, the method continues with a step of generating a plurality of secondary auxiliary treatment plans. For example, one auxiliary treatment plan is generated using a margin equal to zero, no blockings and arc-weights which enable the lower and/or upper dose prescription limit (e.g. only the lower dose prescription limit) to be met. Other auxiliary treatment plans may then be generated based on this one auxiliary treatment plan by changing one (or more) of the margins, arc-weights and blockings of the one auxiliary treatment plan, using heuristic, stochastic and/or gradient-based exploration. The generation of the auxiliary treatment plans and a subsequent selection of one of the secondary auxiliary treatment plans is in other words performed using heuristic, stochastic and/or gradient-based exploration. Multiple iterations of generating (secondary, tertiary, quaternary . . . ) auxiliary treatment plans and subsequently selecting one of these auxiliary treatment plans may be performed until the method converges (i.e. until the selected auxiliary treatment plan is only little improved with respect to a previously selected auxiliary treatment plan). The "little improvement" may be determined using an objective function. For example, the objective function assigns a rating value to each of the auxiliary treatment plans. In case the rating value of the selected auxiliary treatment plan differs from the rating value of the previously selected auxiliary treatment plan less than a predetermined convergence threshold, the method is considered as converged. In this case, the currently selected auxiliary treatment plan is selected as the treatment plan. The generation of the (secondary, tertiary, quaternary . . . ) auxiliary treatment plans and the subsequent selection of one of these auxiliary treatment plans may be performed using heuristic, stochastic and/or gradient-based exploration, for example based on the aforementioned objective function. A detailed example will be given below.

Figure 8:
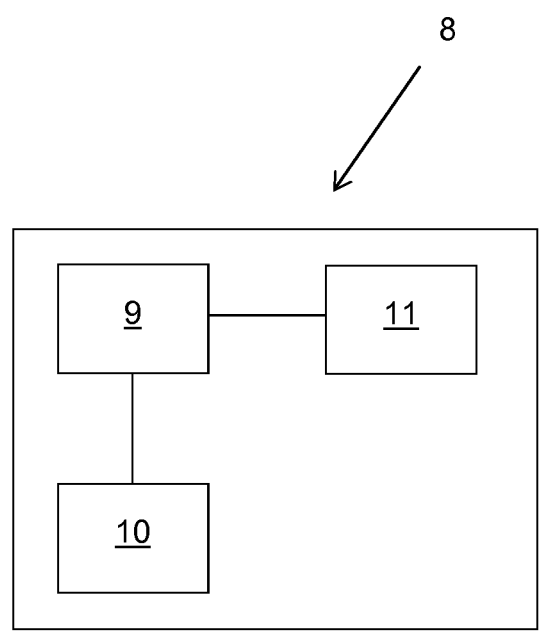
FIG. 8 is a schematic illustration of the system according to the fifth aspect.

FIG. 8 is a schematic illustration of the medical system 8 according to the fifth aspect. The system is in its entirety identified by reference sign 8 and comprises a computer 9, an electronic data storage device (such as a hard disc) 10 for storing at least the patient image data and a medical device 11 (such as a radiation treatment apparatus). The components of the medical system 8 have the functionalities and properties explained above with regard to the fifth aspect of this disclosure.

The invention also relates to the exemplary method as described in the following.

The method aims provide advanced treatment planning for multiple brain metastases including iso-dose line (IDL) prescriptions, allowing the operator to control dose homogeneity/inhomogeneity by prescribing a range of dose values per treated metastasis, and risk structure sparing, allowing the operator to reduce dose in specified volumes of interest.

One can differentiate between three tissue types: target volumes (e.g. the volumes of interest containing the brain metastases which are selected for treatment by irradiation), normal tissue (e.g. the volume of the patient's head surrounding the target) and risk structures (e.g. pre-defined volumes of interest, typically corresponding to vital organs such as brainstem, eye and optical nerve).

The aim of treatment planning is to find an irradiation plan which delivers the prescribed dose values to the target volumes, while minimizing the dose to surrounding normal tissue. Moreover, dose limits can be set for risk structures, to constrain dose to the respective localities.

The method produces treatment plans consisting of dynamic conformal arcs (a treatment modality for linac-based radiation therapy in which the linac head rotates around a patient, utilizing a gantry) with a single iso-center.

Fields are collimated dynamically using a multi-leaf collimator while the gantry of the linac rotates around the patient's head. The fields are shaped according to projections of the metastases (outlines) for a finite set of gantry angles (control points). For each control point, a projected shape (outline) can be either opened or blocked to alter the dose contribution to the irradiation are defined by the projected shape (outline). Moreover, a (e.g. negative or positive) margin can be added to the projected shape (outline) to influence the dose profile. Finally, (a number of) monitor units (arc-weights) must be set per arc (single rotation of the gantry). Monitor units are a measure of beam source (e.g. LINAC) output and influence treatment time/efficiency.

For example, the outline is a feature defining dynamic conformal arcs (DCA). This separates the method from other approaches, for example from volumetric arc therapy (VMAT) approaches. In a sense, VMAT is more sophisticated than DCA (Dynamic Conformal Arc), as it contains a superset of degrees of freedom. At the same time this makes finding a good solution (a treatment plan which sufficiently fits the criteria) intractable. Moreover, VMAT fields tend to be discontinuous and hence potentially decrease the dose calculation accuracy.

It follows that for dynamic conformal arc treatment plan optimization, several degrees of freedom are available:
  (1) Distribution of metastases (targets) to arcs (paths)
  (2) Arc-weights (sum of all (numbers of) monitor units of one arc/path)
  (3) Opening or closing (blocking) of a projected shape (outline) per control point
  (4) Margin per metastasis (target) per arc (path)

Previous solutions for multiple brain metastases provide a solution to this optimization problem by mainly focusing on degrees of freedom (1), (2) and (3). The respective algorithm is tailored to the optimization of a single dose prescription point per metastasis and its application cannot be extended to include feature (A) and (B) as defined below. This patent application proposes a completely novel solution to solve the optimization problem, incorporating all four degrees of freedom (1), (2), (3) and (4). This allows the implementation of the following features (A) and (B).

(A) Iso-Dose Line Prescription Optimization

For each individual metastasis (target), a prescription range can be configured by the operator and may be defined by a lower and higher dose prescription point (lower dose prescription limit and upper dose prescription limit) as follows: The lower point (lower dose prescription limit) corresponds to the minimum dose which should be received in the metastasis (target) under treatment (when following the treatment plan). It is usually prescribed to a volume of 98%-100% of the target volume. The upper dose prescription point (upper dose prescription limit) is a surrogate for the maximum dose, which is usually expressed as the minimum dose received by the 1%-5% of the target volume receiving the highest dose values. The definition of the dose range (e.g. by defining the lower dose prescription limit and upper dose prescription limit) allows clinicians (users) to carefully design iso-dose line prescriptions utilizing homogeneous/inhomogeneous dose distributions. In other words, a user may specify the shape of the function H3 shown in FIG. 4 for one or more targets by defining the points P3a and P3b for each of the one or more targets. As explained above, the use of margins (degree of freedom (4)) influences the spatial dose distribution as shown in FIG. 3. The spatial dose distribution influences the shape of the respective function in the cumulative dose-volume histogram (e.g. the shape of function H3 shown in FIG. 4). Therefore, the treatment plan is determined by optimizing the margins (degree of freedom (4)) to drive homogeneity/inhomogeneity of the dose distribution.

(B) Risk-Structure Sparing Optimization

For each identified risk-structure, a risk structure dose limit can be specified by the operator. A stochastic optimizer iteratively explores fields which can be blocked (i.e. irradiation areas which can be blocked) in order to achieve the provided risk structure dose limit, while satisfying the prescription doses (upper and/or lower dose prescription limit) to the metastases (targets) as reasonably achievable.

An instance of the degrees of freedom (3) and (4) is called an arc configuration in the remainder of this document.

An objective function is used to express the "goodness" (the degree to which an auxiliary treatment plan matches the criteria to be fulfilled by the treatment plan) of a given dose distribution (of an auxiliary treatment plan) during all optimization stages. The function is composed (e.g. as weighted sum) of the following factors:
  i. (e.g. quadratic) deviation of lower dose prescription point (per metastasis) (first difference as described by the first difference data)
  ii. (e.g. quadratic) deviation of upper dose prescription point (per metastasis) (second difference as described by the second difference data)
  iii. Gradient index (e.g. determined based on *A simple dose gradient measurement tool to complement the conformity index* (Ian Paddick, M. Sc., and Bodo Lippitz, M. D., in J Neurosurg (Suppl) 105:194-201, 2006)), defined as the relative volume of normal tissue dose outside of the treated target volume exceeding a dose level (per metastasis) (relation between first volume and second volume as described by the gradient index data)
  iv. (e.g. quadratic) deviation of risk structure constraint (per risk structure constraint) (third difference as described by the third difference data)
  v. Total monitor units (sum of all arc weights as described by the total arc weight data)

Note that several targets and/or risk structure may need to be assessed. This may be done by minimizing an objective function for each of the targets and/or risk structures individually or by combining each of the targets and risk structures in the objective function at the same time. For example, factors i. and ii. may be weighted between all targets and factor iv. may be weighted between all risk structures. The objective function is to be minimized. For example, the value of the objective function for a first auxiliary treatment plan is lower than the value of the objective function of a second treatment plan. In this case, the first auxiliary treatment plan has a higher degree of "goodness" (e.g. has a higher value of the degree to which the auxiliary treatment plan matches the criteria to be fulfilled by the treatment plan).

Factors i. and ii. articulate the deviation to the homogeneous/inhomogeneous prescription. For example, factor i. defines the first difference as described by the first difference data whilst factor ii. defines the second difference as described by the second difference data.

Factor iii. indicates the normal tissue volume exceeding a threshold dose (e.g. in the form of a gradient index). A meaningful threshold may contain a range of high dose-values, which may be defined relatively to the lower dose prescription point (the lower dose prescription limit). A threshold of 50-90%, for example 80%, of the lower dose prescription limit can be chosen as the threshold dose. As described above, a first predetermined sum and a second predetermined sum may be used to determine the relation between the first volume and the second volume which is described by the gradient index data (correlated with factor iii.). The first predetermined sum can be equal to 50-90%, for example 80%, of the lower dose prescription limit.

Factor iv. penalizes violated risk-structure constraints. For example, the deviation of risk structure constraint is expressed as third difference as described by the third difference data.

Factor v. influences treatment time and/or efficiency. For example, a beam source (e.g. LINAC) needs more time to deliver more (a greater number of) monitor units. Treatment time and (number of) monitor units are (very roughly) proportional. The total (number of) monitor units are for example the sum of all arc weights as described by the total arc weight data of the auxiliary treatment plan.

At least the factors ii., iii. and iv. were not included in the previous solutions for multiple brain metastases, but are required to implement the features (A) and (B) mentioned above.

The degrees of freedom (1) to (4) described above result in a large search space. Many combinations of these degrees of freedom are possible for a treatment plan. To make searching (determining the treatment plan, e.g. by selecting one of the auxiliary treatment plans as the treatment plan) feasible, a fast arc-weight optimization algorithm is used to optimize degree of freedom (2) independently for a given arc configuration (for a given instance of the degrees of freedom (3) and (4)): At several arc configuration optimization stages (each stage defined by a generated set of auxiliary treatment plans, e.g. a first optimization stage for the auxiliary treatment plans, a second optimization stage for the secondary auxiliary treatment plans and so on), the individual arc-weights (the arc-weights of the individual paths (arcs) of the (secondary, tertiary, . . . ) auxiliary treatment plan; the arc-weights are for example each expressed as a sum of (the number of) monitor units) are optimized stochastically by minimization of the aforementioned objective function.

To enable fast dose computation, a dose-influence approach is used. It is assumed that the total dose (e.g. described by the total irradiation dose data) can be composed linearly as sum of all individual subfield doses (the sum of all simulated irradiation doses received by (one or more of/all of) the voxels of (generated from) the patient image data (e.g. the voxels of a target) when following the (secondary, tertiary . . . ) auxiliary treatment plan, i.e. the sum of all simulated irradiation doses for all control points of the (secondary, tertiary . . . ) auxiliary treatment plan). This is related to the "beamlet approach", which is widely used for treatment plan optimization. However, instead of dose computation for rectangular subfields, the dose contribution is computed for a set of target volume projections (irradiation areas based on auxiliary outlines) for various margins.

Prior to the arc configuration optimization, dose contributions are pre-computed (the irradiation data is determined) for each metastasis (target), for each margin setting to be explored (margins), for each control point of an arc (path). The optimization algorithm allows for evaluation of full dose distributions for any arc configuration by fast addition of a set of these dose contributions. The algorithm is able to compute doses (determine the irradiation data) and evaluate the objective function (e.g. determine the rating data and select one of the auxiliary treatment plans) thousands of times per second by exploiting parallel computing.

During arc configuration optimization, regular recalibration is advantageous to maintain a stable optimization result. This is for example implemented by computing the dose for a whole arc and comparing it to the approximated dose contribution.

Figure 9:
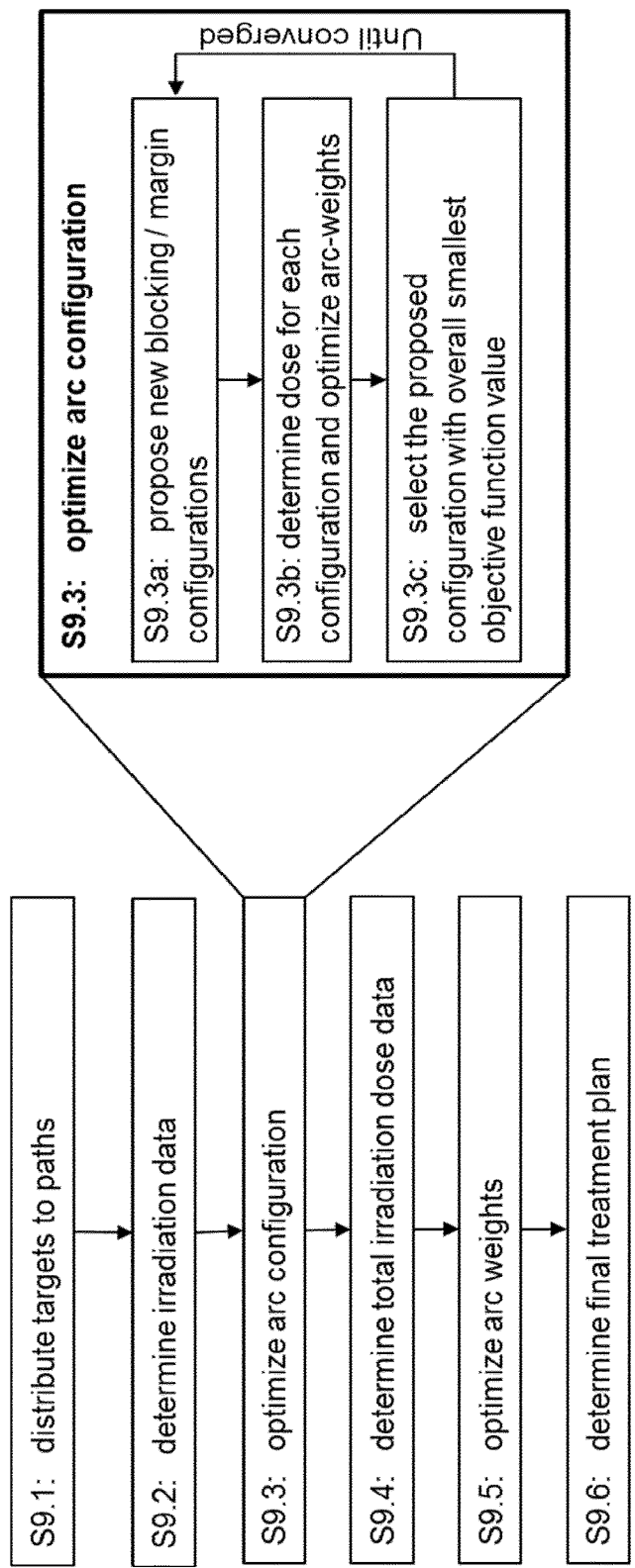
FIG. 9 illustrates the steps of an example of the method according to the first aspect.

FIG. 9 illustrates the steps of an example of the method according to the first aspect. The algorithm for multiple metastases treatment plan optimization (determining the treatment plan) according to this example of the method is summarized below with reference to FIG. 9.

In step S9.1, all metastases (targets) are distributed to a preset number of arcs (paths). The algorithm for this target distribution can be adapted from commonly known methods. The metastases (targets) are for example selected such that unnecessary leaf gaps (distances between collimator leaves and the (auxiliary) outlines) are avoided to reduce the normal tissue dose. The metastases (targets) are for example selected such that the number of patient support device angles (relative positions between the patient support device and the irradiation direction) per metastasis (target) is maximized for optimal dose conformity.

Instead of a brute-force approach, a stochastic search strategy is used to make the arc configuration optimization feasible for a large number of metastases (targets) and/or arcs (paths).

After determination of the metastasis-to-arc distribution, the irradiation data can be determined for individual control points of the arcs and for several margins as described above (step S9.2). To improve computation speed, this process is e.g. parallelized over control points. The result is for example stored in a main memory (e.g. a transitory or a non-transitory storage medium).

An arc configuration optimization loop explores opening and closing (blocking) of fields per metastasis (target) per control point and various margins (step S9.3 comprising sub-steps S9.3a, S9.3b and S9.3c).

After determination of the optimal blockings/margins and arc-weights, final arcs are constructed and the respective dose contributions (irradiation doses, e.g. as described by the sum of all simulated irradiation doses received by the at least one voxel of the patient image data for each individual arc when following the auxiliary treatment plan/when using the determined optimal blockings, margins and arc-weights) are computed (S9.4). For example, the total irradiation dose data is determined for each of the arcs (paths) individually in this step, i.e. the total irradiation dose data describes the sum of all simulated irradiation doses received by at least one voxel of the patient image when using the selected treatment plan, for each of the paths of the selected treatment plan individually (dose per arc).

Subsequently, a final arc-weight optimization is performed (step S9.5) to fine-tune the final dose distribution, using the same search algorithm and objective function as above. During this step, the arc-weights are optimized once more. However, the leaves (and other machine parameters) are not changed (i.e. the blockings and margins are kept constant). This ensures that the dose determined in step S9.4 remains accurate during this step.

Finally, the treatment plan is generated in step S9.6 (e.g. determined) and available for evaluation, modification, saving and export.

Finding the optimal clipping and margin configuration to optimize the arc configuration (S9.3) can be formulated as a stochastic optimization problem, which iteratively proposes random configurations based on the previous best result.

To improve the convergence (and hence runtime) of the algorithm, new configurations can be proposed in sub-step S9.3a heuristically based on deviations from the lower and upper dose prescription points (lower and upper dose prescription limits):

- If the dose (as described by the target dose data) in the lower and upper prescription point (the lower and the upper dose prescription limits) of a metastasis (target) is exceeded (e.g. by a threshold dose tolerance t1), then a field (an irradiation area of a given control point) can be blocked (blocking).
- If dose (as described by the target dose data) in the upper prescription point (upper dose prescription limit) of a metastasis (target) is exceeded (by a threshold dose tolerance t2) and the lower prescription point (lower dose prescription limit) is satisfied (within a threshold dose tolerance t3), then a margin can be increased (a larger margin can be used for some or all of the control points, e.g. when generating the next auxiliary treatment plans).
- If dose (as described by the target dose data) in the upper prescription point (the upper dose prescription limit) is less than prescribed (by a threshold dose tolerance t4) and the lower prescription point (lower dose prescription limit) is satisfied (within a threshold dose tolerance t5), then a margin can be decreased (a smaller margin can be used for some or all of the control points, e.g. when generating the next auxiliary treatment plans).
- If dose (as described by the target dose data) in the lower prescription point (lower dose prescription limit) of a metastasis (target) is exceeded (by a threshold dose tolerance t6) and the upper prescription point (upper dose prescription limit) is satisfied (within a threshold dose tolerance t7), then a field (an irradiation area of a given control point) can be blocked (blocking) and/or a margin can be decreased (a smaller margin can be used for some or all of the control points, e.g. when generating the next auxiliary treatment plans).

A value of t1, t2, t3, t4, t5, t6 and/or t7 may be picked from the range 1-5%, for example 2%. This value represents a trade-off between good treatment plans and optimization time. Only considering heuristic configurations may result in the optimizer getting stuck in local minima. Therefore, configurations based on random margin changes might be proposed in addition to the heuristic configurations.

Changing an arc configuration requires re-optimization of the arc-weights. To take advantage of multi-core CPU architectures, a new algorithm is used to optimize arc-weights quickly for several proposed configurations in parallel (sub-step S9.3b). The proposed configurations from sub-step S9.3a are sorted by dose deviation (e.g. using the first difference, the second difference) and added to a priority queue.

This queue is subdivided in batches of a fraction of the number of threads. For N threads and M proposed heuristic configurations, another N-M random configurations are added. The ratio between heuristically and randomly proposed configurations depends on the total number of threads: for example at least one random configuration is proposed. For the initial phase of the arc configuration optimization, a 1:1 ratio between heuristically and randomly proposed configurations ratio can be expected to yield good results. However, other ratios may be used.

Arc-weight optimization is started in parallel for resulting batches of N configurations based on rating data (e.g. rating data is determined for the proposed configurations which represent the auxiliary treatment plans, for example the rating data is determined based on the aforementioned objective function). For example, the target dose data is determined and the rating data is determined on the first difference and/or the second difference. For example, the normal tissue dose data is determined and the rating is determined on the relation described by the gradient index data (which is for example determined based on the normal tissue dose data). For example, risk structure dose data is determined and the rating data is determined based on the third difference.

If an objective function improvement is found in a batch, the rest of the priority queue is neglected. If not, the rest of the subdivided queue is optimized consecutively. For example, if no overall improvement of the objective function could be found, the optimization problem is considered converged.

After the algorithm converges (the optimization algorithm of step S9.3 including the sub-steps S9.3a, S9.3b and S9.3c), it is restarted (not indicated in FIG. 9) with a different ratio (refinement step). The converging of the optimization algorithm may be determined by selecting the proposed configuration with the overall smallest objective function value from the proposed configurations (e.g. selection one of the auxiliary treatment plans). In case this objective function value changes from one iteration to the other less than a predetermined threshold, it is determined that the algorithm has converged.

As no heuristic configurations can be proposed (optimization algorithm has converged, i.e. no better configurations can be proposed heuristically), a 100% randomly changed configuration batch is started. This might introduce new deviations from the lower and upper dose prescription point (lower and upper dose prescription limit) and hence new heuristic configuration changes become available. As it is expected that the number of heuristic configurations is small at this stage, the ratio can be increased in favor of the randomly proposed configurations (e.g. to a ratio of 1:3 between heuristically and randomly proposed configurations). The number of restarts is for example restricted to limit optimization time. For example, the number of restarts is restricted to 2 to yield good results.

For each configuration, the respective pre-computed irradiation doses described by the irradiation data are summed over each of the arcs (paths) of the determined treatment plan (the selected configuration) in sub-step S9.3b in a cache friendly manner. Arc-weights can afterwards be optimized stochastically in sub-step S9.3b. For each arc-weight combination under consideration, the dose in the prescription points is computed (e.g. the target dose), along with normal tissue dose and all terms of the objective function (e.g. risk structure dose).

The determined irradiation data is independent on the lower/upper dose prescription limits and must be computed only once. Therefore, after initial optimization, the operator can interact with the optimization result: the operator is given the flexibility to explore several prescriptions in terms of dose and volume. In this case steps S9.1 and S9.2 are omitted. A new graphical user interface solution can be implemented to support an interactive planning workflow.

The invention claimed is:
1. A computer-implemented method of determining a treatment for treating at least one target by emitting irradiation by a beam source through a beam shaping device in an irradiation direction movable around a movable patient support device, the method comprising the following steps:
   acquiring patient image data which describes one or more anatomical body parts of a patient;

acquiring target data which specifies at least one of the one or more anatomical body parts as the at least one target for irradiation;

acquiring position data describing at least one position of the moveable patient support device in relation to the irradiation direction;

determining target projection data based on the target data and the position data,
- wherein the target projection data is determined for the at least one target and for the at least one position of the moveable patient support device in relation to the irradiation direction, and
- wherein the target projection data describes outlines of the at least one target each projected into a plane perpendicular to a corresponding simulated beam direction,
  - wherein the corresponding simulated beam direction is specified by a corresponding position of the at least one position of the moveable patient support device in relation to the irradiation direction;

acquiring margin data describing one or more margins for the at least one target,
- wherein each of the one or more margins is a distance of a corresponding outline of the at least one projected target to a corresponding auxiliary outline correlated with the at least one target;

determining auxiliary outline data based on the target projection data and the margin data,
- wherein the auxiliary outline data is determined for the at least one target, for the at least one position of the moveable patient support device in relation to the irradiation direction and for the one or more margins, and
- wherein the auxiliary outline data describes one or more auxiliary outlines correlated with the at least one target, for the one or more margins;

determining beam shaping device data based on the auxiliary outline data,
- wherein the beam shaping device data describes one or more configurations of the beam shaping device which enable irradiation of one or more irradiation areas specified by the one or more auxiliary outlines;

determining irradiation data based on the patient image data and the beam shaping device data,
- wherein the irradiation data is determined for at least one voxel of the patient image data and for the one or more configurations of the beam shaping device, and
- wherein the irradiation data describes a simulated irradiation dose received by the at least one voxel, for each of the one or more configurations of the beam shaping device described by the beam shaping device data;

acquiring constraint data describing criteria to be fulfilled by the treatment, the treatment
- specifying one or more paths along which the irradiation direction and/or the moveable patient support device shall move during irradiation, wherein the one or more paths are each specified by one or more control points being one or more of the at least one position of the moveable patient support device in relation to the irradiation direction described by the position data,
- specifying, for each of the one or more paths, monitor units to be emitted by the beam source during movement along each of the one or more paths and
- specifying a corresponding configuration of the beam shaping device for each of the one or more control points;

determining the treatment based on the irradiation data and the constraint data,
- wherein an arc weight is defined as a sum of the monitor units to be emitted by the beam source during movement along one of the one or more paths, a blocking is defined as a configuration of the beam shaping device preventing irradiation to an irradiation area at a corresponding control point, and
- wherein the treatment is determined based on different combinations of: the one or more margins, arc weights for the one or more paths, and blockings for the one or more configurations of the beam shaping device; and causing the irradiation to be emitted by the beam source according to the treatment.

2. The method of claim 1, further comprising the following step:
acquiring path data describing the one or more paths each specified by the one or more control points being one or more of the at least one position of the moveable patient support device in relation to the irradiation direction described by the position data,
wherein the one or more paths specified by the treatment are the one or more paths described by the path data.

3. The method of claim 1, further comprising the following step:
acquiring blocking data describing the blockings for the one or more paths specified by the treatment.

4. The method according to claim 1, wherein the position data describes only the one or more control points specifying the one or more paths specified by the treatment.

5. The method according to claim 1, wherein the constraint data describes at least one of the following:
a lower dose prescription limit specifying a minimum value of a sum of all simulated irradiation doses received by a first predetermined volumetric percentage of a target, of the at least one target, when following the treatment; and
an upper dose prescription limit specifying a minimum value of the sum of all simulated irradiation doses received by a second predetermined volumetric percentage of the target when following the treatment.

6. The method according to claim 5, wherein the treatment is determined by performing the following steps:
generating a plurality of auxiliary treatment steps, based on the different combinations of the one or more margins, the arc weights and the blockings; and
for each of the plurality of auxiliary treatment steps,
determining target dose data based on the irradiation data,
wherein the target dose data is determined for the at least one target, and
wherein the target dose data describes the sum of all simulated irradiation doses received by the at least one target when following the plurality of auxiliary treatment steps, and
determining rating data at least based on the target dose data and the constraint data,
wherein the rating data describes a degree to which the plurality of auxiliary treatment steps match the criteria to be fulfilled by the treatment; and
selecting one of the plurality of auxiliary treatment steps as the treatment based on the rating data.

7. The method according to claim 6, further comprising the following steps performed for each of the plurality of auxiliary treatment steps after having determined the target dose data:
   determining first difference data based on the constraint data and the target dose data,
      wherein the first difference data is determined for the at least one target,
      wherein the first difference data describes a first difference between a lower dose prescription limit and the sum of all simulated irradiation doses received by the at least one target when following the plurality of auxiliary treatment steps;
   determining second difference data based on the constraint data and the target dose data,
      wherein the second difference data is determined for the at least one target,
      wherein the second difference data describes a second difference between an upper dose description limit and the sum of all simulated irradiation doses received by the at least one target when following the plurality of auxiliary treatment steps; and
   determining total arc weight data based on the monitor units to be emitted by the beam source during movement along the one or more paths specified by the treatment having the plurality of auxiliary treatment steps,
      wherein the total arc weight data describes a sum of all arc weights of all paths specified by the plurality of auxiliary treatment steps,
      wherein a degree to which the plurality of auxiliary treatment steps match the criteria to be fulfilled by the treatment is specified at least by the first difference described by the first difference data, the second difference described by the second difference data and the sum of all arc weights described by the total arc weight data.

8. The method according to claim 6, further comprising the following step performed for each of the plurality of auxiliary treatment steps after having determined the target dose data:
   determining normal tissue dose data based on the irradiation data,
      wherein the normal tissue dose data is determined for the at least one target,
      wherein the normal tissue dose data describes the sum of all simulated irradiation doses received by normal tissue when following the plurality of auxiliary treatment steps,
         wherein the normal tissue includes all of the one or more anatomical body parts of the patient described by the patient image data and
         wherein the rating data is determined furthermore based on the normal tissue dose data.

9. The method according to claim 8, further comprising the following steps performed for each of the plurality of auxiliary treatment steps after having determined the normal tissue dose data:
   determining gradient index data based on the normal tissue dose data,
      wherein the gradient index data describes a relation between
         a first volume of the normal tissue which receives at least a first predetermined sum of all simulated irradiation doses when following the plurality of auxiliary treatment steps and
         a second volume of the normal tissue which receives at least a second predetermined sum of all simulated irradiation doses when following the plurality of auxiliary treatment steps,
      wherein a degree to which the plurality of auxiliary treatment steps matches the criteria to be fulfilled by the treatment is specified furthermore by the relation between the first volume and the second volume described by the gradient index data.

10. The method according to claim 6, further comprising the following step:
   acquiring risk structure data which designates at least one of the one or more anatomical body parts as at least one risk structure for irradiation,
      wherein the constraint data describes at least one risk structure dose limit specifying a simulated irradiation dose received by the at least one risk structure.

11. The method according to claim 10, further comprising the following step performed for each of the plurality of auxiliary treatment steps before determining the rating data:
   determining risk structure dose data based on the irradiation data and the risk structure data,
      wherein the risk structure dose data is determined for the at least one risk structure,
      wherein the risk structure dose data describes the sum of all simulated irradiation doses received by the at least one risk structure when following the plurality of auxiliary treatment steps, and
      wherein the rating data is determined furthermore based on the risk structure dose data.

12. The method according to claim 11, further comprising the following step performed for each of the plurality of auxiliary treatment steps after having determined the risk structure dose data:
   determining difference data based on the constraint data and the risk structure dose data,
      wherein the difference data is determined for the at least one risk structure
      wherein the difference data describes a difference between the at least one risk structure dose limit and the sum of all simulated irradiation doses received by the at least one risk structure when following the plurality of auxiliary treatment steps,
      wherein a degree to which the plurality of auxiliary treatment steps match the criteria to be fulfilled by the treatment is specified furthermore by the difference described by the difference data.

13. A non-transient computer program which, when running on a computer or when loaded onto a computer, causes the computer to perform the method steps of the method according to claim 6.

14. A medical system, comprising:
   at least one computer having at least one processor operable to execute the steps of a computer program comprising:
      acquiring patient image data which describes one or more anatomical body parts of a patient;
      acquiring target data which specifies at least one of the one or more anatomical body parts as at least one target for irradiation;
      acquiring position data describing at least one position of a patient support device in relation to an irradiation direction;
      determining target projection data based on the target data and the position data, wherein the target projection data is determined for the at least one target and for the at least one position of the patient support device in relation to the irradiation direction, wherein the target projection data describes outlines of the at least one target projected into a plane perpendicular to a corresponding simulated beam direction, and wherein the corresponding simulated beam direction is specified by a corresponding position of the at least one position of the patient support device in relation to the irradiation direction;

acquiring margin data describing one or more margins for the at least one target, wherein a margin, of the one or more margins, is a distance of a corresponding outline of the at least one projected target to a corresponding auxiliary outline correlated with the at least one target;

determining auxiliary outline data based on the target projection data and the margin data, wherein the auxiliary outline data is determined for the at least one target, for the at least one position of the patient support device in relation to the irradiation direction and for the one or more margins, and wherein the auxiliary outline data describes one or more auxiliary outlines correlated with the at least one target, that respectively corresponds to an outline of the at least one projected target;

determining beam shaping device data based on the auxiliary outline data, wherein the beam shaping device data describes one or more configurations of a beam shaping device which enable irradiation of one or more irradiation areas specified by the one or more auxiliary outlines;

determining irradiation data based on the patient image data and the beam shaping device data, wherein the irradiation data is determined for at least one voxel of one or more images of the patient image data and for the one or more configurations of the beam shaping device, and wherein the irradiation data describes a simulated irradiation dose received by the at least one voxel, for each of the one or more configurations of the beam shaping device described by the beam shaping device data;

acquiring constraint data describing criteria to be fulfilled by a treatment, the treatment specifying one or more paths along which the irradiation direction and/or the patient support device shall move during irradiation, wherein the one or more paths are each specified by one or more control points being one or more of the at least one position of the patient support device in relation to the irradiation direction described by the position data, specifying, for each of the one or more paths, monitor units to be emitted by a beam source during movement along each of the one or more paths and specifying a corresponding configuration of the beam shaping device for each of the one or more control points; and determining the treatment based on the irradiation data and the constraint data, wherein an arc weight is defined as a sum of the monitor units to be emitted by the beam source during movement along one of the one or more paths, a blocking is defined as a configuration of the beam shaping device preventing irradiation to an irradiation area at a corresponding control point, of the one or more control points, and wherein the treatment is determined based on different combinations of:
the one or more margins,
arc weights for the one or more paths, and
blockings for the one or more configurations of the beam shaping device;

at least one electronic data storage device storing at least the patient image data; and a medical device for carrying out a medical procedure on the patient, wherein the at least one computer is operably coupled to the at least one electronic data storage device to acquire, from the at least one electronic data storage device, at least the patient image data, and wherein the at least one computer is operably coupled to the medical device to issue a control signal to the medical device to control an operation of the medical device based on the treatment.

15. The system according to claim 14, wherein the medical device comprises:

a radiation treatment apparatus comprising the beam source, the beam shaping device and the patient support device, wherein the at least one computer is operably coupled to the radiation treatment apparatus for issuing a control signal to the radiation treatment apparatus for controlling, based on the treatment, at least one of:
an operation of the beam source,
an operation of the beam shaping device, or
the at least one position of the patient support device.

* * * * *